(12) United States Patent
Funaro et al.

(10) Patent No.: US 8,153,129 B2
(45) Date of Patent: Apr. 10, 2012

(54) ANTIBODIES AGAINST HUMAN CYTIMEGALOVIRUS (HCMV)

(75) Inventors: Ada Funaro, Turin (IT); Giorgio Gribaudo, Villafalletto (IT); Santo Landolfo, Turin (IT)

(73) Assignee: Ribovax Biotechnologies S.A., Petit-Lancy (CH)

( * ) Notice: Subject to any disclaimer, the term of this patent is extended or adjusted under 35 U.S.C. 154(b) by 211 days.

(21) Appl. No.: 12/519,236

(22) PCT Filed: Dec. 17, 2007

(86) PCT No.: PCT/EP2007/064094
§ 371 (c)(1),
(2), (4) Date: Oct. 28, 2009

(87) PCT Pub. No.: WO2008/071806
PCT Pub. Date: Jun. 19, 2008

(65) Prior Publication Data
US 2010/0040602 A1 Feb. 18, 2010

(30) Foreign Application Priority Data

Dec. 15, 2006 (WO) ................. PCT/EP2006/069780
Jun. 20, 2007 (EP) ..................... 07110693

(51) Int. Cl.
*A61K 39/42* (2006.01)
*A61K 48/00* (2006.01)
*C07K 16/08* (2006.01)
*C12N 15/13* (2006.01)
*C12N 5/10* (2006.01)
*C12Q 1/70* (2006.01)

(52) U.S. Cl. ............. 424/142.1; 424/147.1; 530/388.15; 530/388.3; 530/389.4; 536/23.53; 514/44 R; 435/320.1; 435/339; 435/328; 435/252.3; 435/5

(58) Field of Classification Search ........................ None
See application file for complete search history.

(56) References Cited

FOREIGN PATENT DOCUMENTS

WO WO 2004/076677 9/2004
WO WO 2006/124269 11/2006

OTHER PUBLICATIONS

Paul, Fundamental Immunology, (textbook), 1993, pp. 292-295, under the heading "Fv Structure and Diversity in Three Dimensions".*
International Search Report in PCT/EP2007/064094 dated May 6, 2008.
Written Opinion in PCT/EP2007/064094 dated May 6, 2008.
Ermel, et al., "Molecular Analysis of Rheumatoid Factors Derived from Rheumatoid Synovium Suggests an Antigen-Driven response in Inflamed Joints," *Arthritis and Rheumatism*, Mar. 1993, 380-388, vol. 36, No. 3.
Steenbakkers et al., "Efficient generation of human anti-cytomegalovirus IgG monoclonal antibodies from preselected antigen-specific B cells," *Hybridomas*, Oct. 1993, 166-173, vol. 4.

* cited by examiner

*Primary Examiner* — Mary E Mosher
(74) *Attorney, Agent, or Firm* — Marshall, Gerstein & Borun LLP

(57) ABSTRACT

The present invention provides novel antibody sequences that bind human cytomegalovirus (hCMV) and neutralize hCMV infection. The novel sequences can be used for the medical management of hCMV infections, in particular for preparing pharmaceutical compositions to be used in the prophylactic or therapeutic treatment of hCMV infections.

20 Claims, 10 Drawing Sheets

Fig. 1
A)
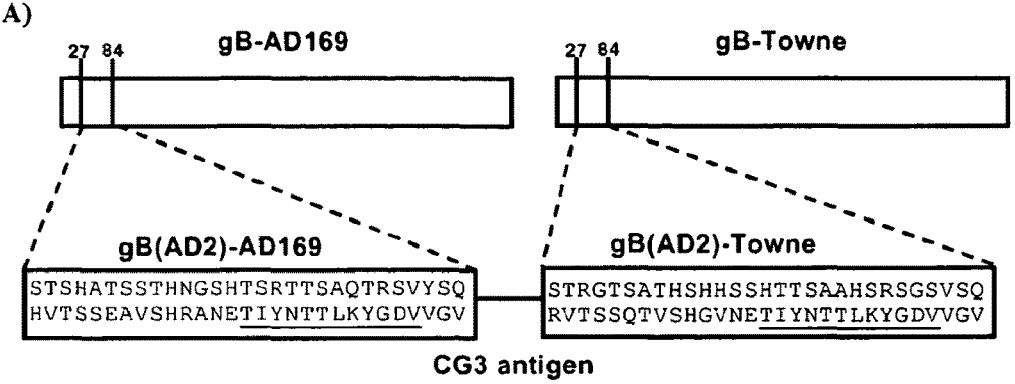
CG3 antigen
B)
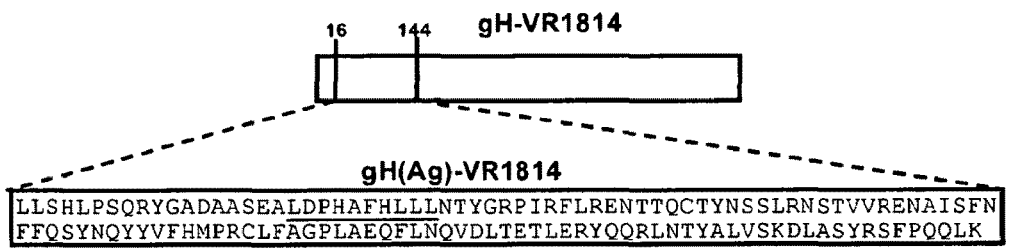

Fig. 4
A)
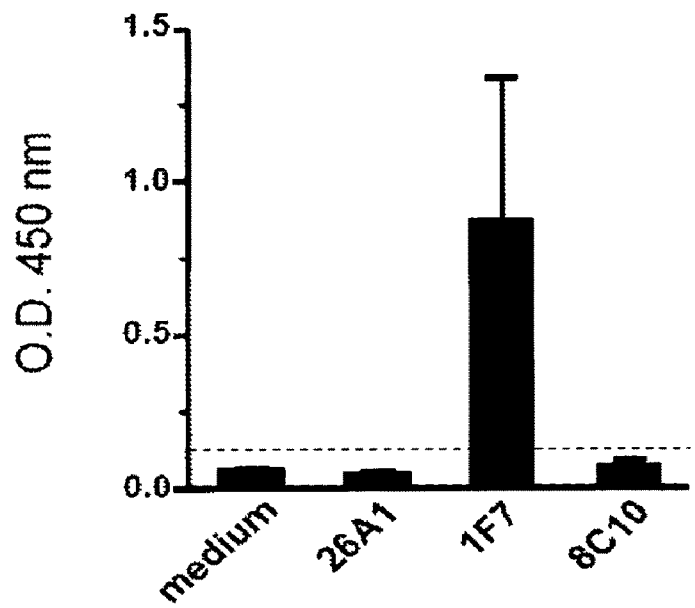
B)
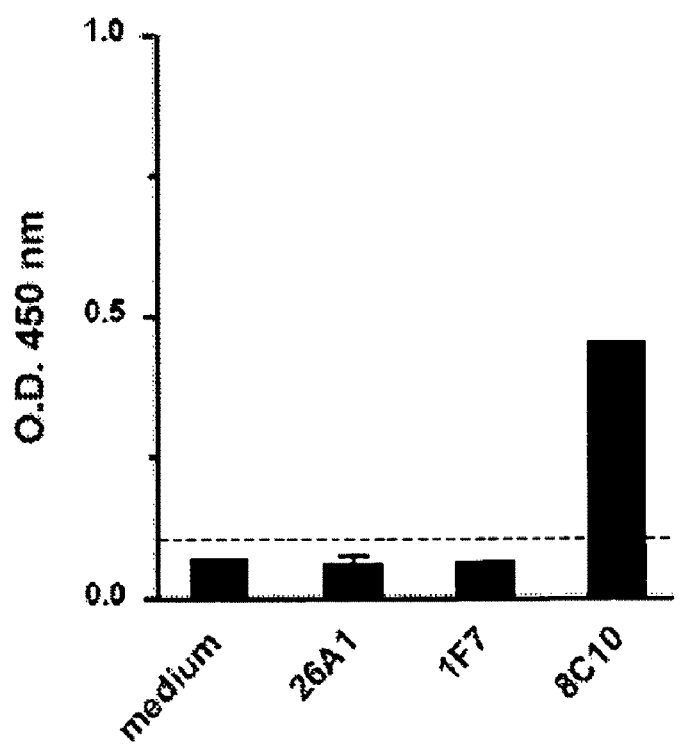

```
                    10                              20
 .  .  .  .  .  .  .  .  .  !  .  .  .  .  .  .  .  .  .  !
 Q  V  Q  L  Q  E  S  G  P  G  L  V  K  P  S  Q  T  L  S  L
caggtgcagctgcaggagtcgggcccaggactggtgaagccttcacagaccctgtccctc 30                              40
 .  .  .  .  .  .  .  .  .  !  .  .  .  .  .  .  .  .  .  !
 I  C  T  V  S  G  G  S  V  S  S  G  G  D  Y  W  T  W  I  R
atatgcactgtctctggtggctccgtcagcagtggtggtgactactggacctggatccgc 50                              60
 .  .  .  .  .  .  .  .  .  !  .  .  .  .  .  .  .  .  .  !
 Q  H  P  G  K  G  L  E  W  L  G  Y  I  H  S  S  G  N  I  F
cagcacccagggaagggcctggagtggcttgggtacatccattccagtgggaatatcttc 70                              80
 .  .  .  .  .  .  .  .  .  !  .  .  .  .  .  .  .  .  .  !
 Y  N  P  S  L  K  S  R  L  T  L  S  M  D  T  S  K  N  Q  F
tacaacccgtccctcaagagtcgactgaccttatcaatggacacgtctaagaaccaattc 90                             100
 .  .  .  .  .  .  .  .  .  !  .  .  .  .  .  .  .  .  .  !
 F  L  K  L  T  S  V  T  A  A  D  T  A  V  Y  Y  C  A  R  V
ttcctgaagttgacctctgtgactgccgcggacacggccgtatattactgtgcgagagtc 110                             120
 .  .  .  .  .  .  .  .  .  !  .  .  .  .  .  .  .  .  .  !
 Y  H  K  D  F  V  V  V  P  G  A  F  P  F  E  F  W  F  D  P
tatcataaggattttgtagtagtaccaggtgctttccccttttgaattctggttcgacccc 130
 .  .  .  .  .  .  .  .  .  !  .
 W  G  Q  G  T  L  V  T  V  S  S
tggggccagggaaccctggtcaccgtctcctca
```

B)

```
                  10        20        30        40        50        60
         .........!.........!.........!.........!.........!.........!
VH 26A1  QVQLQESGPGLVKPSQTLSLICTVSGGSVSSGGDYWTWIRQHPGKGLEWLGYIHSSGNIF
                              T       ─────────        E        ─────
                                         HCDR1                  HCDR2
                                                                V   V 70        80        90       100       110       120
         .........!.........!.........!.........!.........!.........!
VH 26A1  YNPSLKSRLTLSMDTSKNQFFLKLTSVTAADTAVYYCARVYHKDFVVVPGAFPFEFWFDP
                     L     T A              ──────────────────────────
                                                     G            S
                                                  HCDR3

130
         .........!.
VH 26A1  WGQGTLVTVSS
             R
```

```
              10                              20
 S  Y  V  L  T  Q  P  P  S  V  S  V  A  P  G  Q  T  A  R  I
tcctatgtgctgactcagccaccctcggtgtcagtggccccaggacagacggccaggatt 30                              40
 P  C  G  G  N  E  I  G  S  K  S  V  H  W  Y  Q  Q  K  P  G
gccctgcgggggaacgagattggaagtaagagtgtccactggtaccagcagaagccaggc 50                              60
 Q  A  P  V  L  V  V  H  D  D  S  D  R  P  S  G  I  P  D  R
caggcccctgtgctggtcgtccatgatgacagcgaccggccctcagggatccctgaccga 70                              80
 F  S  G  S  N  S  G  N  T  A  L  T  I  S  R  V  E  A  G
ttctctggctccaactctgggaacacggccaccctgaccatcagcagggtcgaagccggg 90                             100
 D  E  A  D  Y  Y  C  Q  V  W  D  S  G  S  D  H  V  V  F
gatgaggccgactattactgtcaggtgtgggatagtggtagtgatcatcatgtggtattc 110
 G  G  G  T  K  L  T  V  L  G
ggcggagggaccaagctgaccgtcctaggt
```

B)

```
               10        20        30        40        50        60
               |.........|.........|.........|.........|.........|.........|
VL 26A1  SYVLTQPPSVSVAPGQTARIPCGGNEIGSKSVHWYQQKPGQAPVLVVHDDSDRPSGIPDR
                                  LCDR1                    LCDR2

70        80        90       100       110
               |.........|.........|.........|.........|........|
VL 26A1  FSGSNSGNTATLTISRVEAGDEADYYCQVWDSGSDHHVVFGGGTKLTVLG
                                  LCDR3
```

Fig. 7

```
atgaacatactgtggagcatgctcctgctggtggcagctcccagatgggtcctgtcccag
 M  N  I  L  W  S  M  L  L  L  V  A  A  P  R  W  V  L  S  Q   20
gtgcagctgcaggagtcgggcccaggactggtgaagccttcacagaccctgtccctcata
 V  Q  L  Q  E  S  G  P  G  L  V  K  P  S  Q  T  L  S  L  I   40
tgcactgtctctggtggctccgtcagcagtggtggtgactactggacctggatccgccag
 C  T  V  S  G  G  S  V  S  S  G  G  D  Y  W  T  W  I  R  Q   60
cacccagggaaggcctggagtggcttgggtacatccattccagtgggaatatcttctac
 H  P  G  K  G  L  E  W  L  G  Y  I  H  S  S  G  N  I  F  Y   80
aacccgtccctcaagagtcgactgaccttatcaatggacacgtctaagaaccaattcttc
 N  P  S  L  K  S  R  L  T  L  S  M  D  T  S  K  N  Q  F  F  100
ctgaagttgacctctgtgactgccgcggacacggccgtatattactgtgcgagagtctat
 L  K  L  T  S  V  T  A  A  D  T  A  V  Y  Y  C  A  R  V  Y  120
cataaggattttgtagtagtaccaggtgctttccccttTgaattctggttcgaccCctgg
 H  K  D  F  V  V  V  P  G  A  F  P  F  E  F  W  F  D  P  W  140
ggccagggaaccctggtcaccgtctcctcaggatccgcctccaccaagggcccatcggtc
 G  Q  G  T  L  V  T  V  S  S  G  S  A  S  T  K  G  P  S  V  160
ttccccctggcaccctcctccaagagcacctctggggGcacagcggccctgggctgcctg
 F  P  L  A  P  S  S  K  S  T  S  G  G  T  A  A  L  G  C  L  180
gtcaaggactacttccccgaaccggtgacggtgtcgtggaactcaggcgccctgaccagc
 V  K  D  Y  F  P  E  P  V  T  V  S  W  N  S  G  A  L  T  S  200
ggcgtgcacaccttcccggctgtcctacagtcctcaggactctactccctcagcagcgtg
 G  V  H  T  F  P  A  V  L  Q  S  S  G  L  Y  S  L  S  S  V  220
gtgaccgtgccctccagcagcttgggcacccagacctacatctgcaacgtgaatcacaag
 V  T  V  P  S  S  S  L  G  T  Q  T  Y  I  C  N  V  N  H  K  240
cccagcaacaccaaggtggacaagaaagttgagcccaaatcttgtgacaaaactcacaca
 P  S  N  T  K  V  D  K  K  V  E  P  K  S  C  D  K  T  H  T  260
tgcccaccgtgcccagcacctgaactcctggggggaccgtcagtcttcctcttccccccA
 C  P  P  C  P  A  P  E  L  L  G  G  P  S  V  F  L  F  P  P  280
aaacccaaggacaccctcatgatctcccggacccctgaggtcacatgcgtggtggtggac
 K  P  K  D  T  L  M  I  S  R  T  P  E  V  T  C  V  V  V  D  300
gtgagccacgaagaccctgaggtcaagttcaactggtacgtggacggcgtggaggtgcat
 V  S  H  E  D  P  E  V  K  F  N  W  Y  V  D  G  V  E  V  H  320
aatgccaagacaaagccgcgggaggagcagtacaacagcacgtaccgggtggtcagcgtc
 N  A  K  T  K  P  R  E  E  Q  Y  N  S  T  Y  R  V  V  S  V  340
ctcaccgtcctgcaccaggactggctgaatggcaaggagtacaagtgcaaggtctccaac
 L  T  V  L  H  Q  D  W  L  N  G  K  E  Y  K  C  K  V  S  N  360
aaagccctcccagcccccatcgagaaaaccatctccaaagccaaagggcagccccgagaa
 K  A  L  P  A  P  I  E  K  T  I  S  K  A  K  G  Q  P  R  E  380
ccacaggtgtacaccctgcccccatcccgggatgagctgaccaagaaccaggtcagcctg
 P  Q  V  Y  T  L  P  P  S  R  D  E  L  T  K  N  Q  V  S  L  400
acctgcctggtcaaaggcttctatcccagcgacatcgccgtggagtgggagagcaatggg
 T  C  L  V  K  G  F  Y  P  S  D  I  A  V  E  W  E  S  N  G  420
cagccggagaacaactacaagaccacgcctcccgtgctggactccgacggctccttcttc
 Q  P  E  N  N  Y  K  T  T  P  P  V  L  D  S  D  G  S  F  F  440
ctctacagcaagctcaccgtggacaagagcaggtggcagcaggggaacgtcttctcatgc
 L  Y  S  K  L  T  V  D  K  S  R  W  Q  Q  G  N  V  F  S  C  460
tccgtgatgcatgaggctctgcacaaccactacacgcagaagagcctctccctgtctccg
 S  V  M  H  E  A  L  H  N  H  Y  T  Q  K  S  L  S  L  S  P  480
ggtaaatga
 G  K stop                                                    482
```

Fig. 8

```
atggcctggaccgttctcctcctcggcctcctctctcactgcacaggttctgtgacctcc
 M  A  W  T  V  L  L  L  G  L  L  S  H  C  T  G  S  V  T  S   20 tatgtgctgactcagccaccctcggtgtcagtggccccaggacagacggccaggattccc
 Y  V  L  T  Q  P  P  S  V  S  V  A  P  G  Q  T  A  R  I  P   40 tgtgggggggaacgagattggaagtaagagtgtccactggtaccagcagaagccaggccag
 C  G  G  N  E  I  G  S  K  S  V  H  W  Y  Q  Q  K  P  G  Q   60 gcccctgtgctggtcgtccatgatgacagcgaccggccctcagggatccctgaccgattc
 A  P  V  L  V  V  H  D  D  S  D  R  P  S  G  I  P  D  R  F   80 tctggctccaactctgggaacacggccaccctgaccatcagcagggtcgaagccggggat
 S  G  S  N  S  G  N  T  A  T  L  T  I  S  R  V  E  A  G  D  100 gaggccgactattactgtcaggtgtgggatagtggtagtgatcatcatgtggtattcggc
 E  A  D  Y  Y  C  Q  V  W  D  S  G  S  D  H  H  V  V  F  G  120 ggagggaccaagctgaccgtcctaggtcagcccaaggctgccccctcggtcactctgttc
 G  G  T  K  L  T  V  L  G  Q  P  K  A  A  P  S  V  T  L  F  140 ccgccctcctctgaggagcttcaagccaacaaggccacactggtgtgtctcataagtgac
 P  P  S  S  E  E  L  Q  A  N  K  A  T  L  V  C  L  I  S  D  160 ttctacccgggagccgtgacagtggcctggaaggcagatagcagccccgtcaaggcggga
 F  Y  P  G  A  V  T  V  A  W  K  A  D  S  S  P  V  K  A  G  180 gtggagaccaccacacccctccaaacaaagcaacaacaagtacgcggccagcagctatctg
 V  E  T  T  T  P  S  K  Q  S  N  N  K  Y  A  A  S  S  Y  L  200 agcctgacgcctgagcagtggaagtcccacagaagctacagctgccaggtcacgcatgaa
 S  L  T  P  E  Q  W  K  S  H  R  S  Y  S  C  Q  V  T  H  E  220 gggagcaccgtggagaagacagtggccccctacagaatgttcatag
 G  S  T  V  E  K  T  V  A  P  T  E  C  S  stop             234
```

Fig. 9
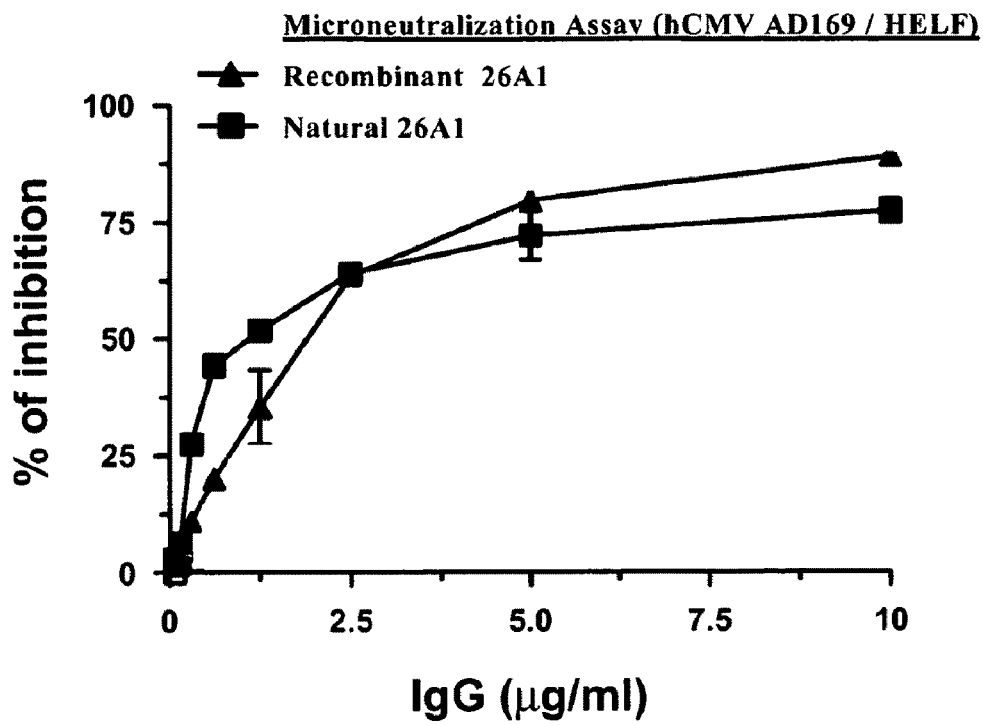
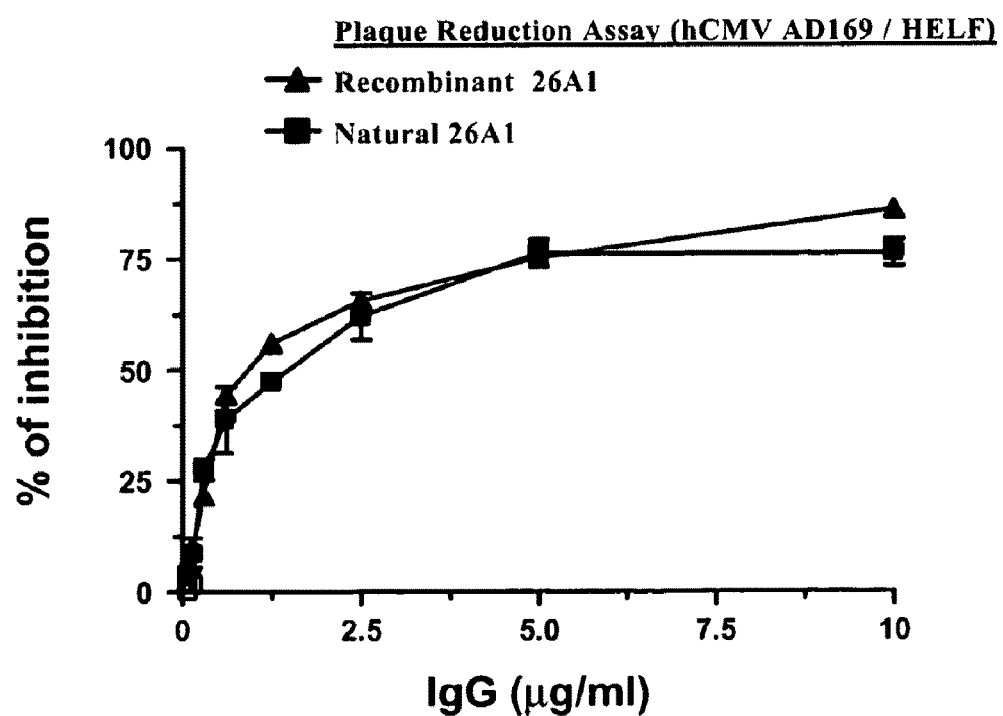

Fig. 10
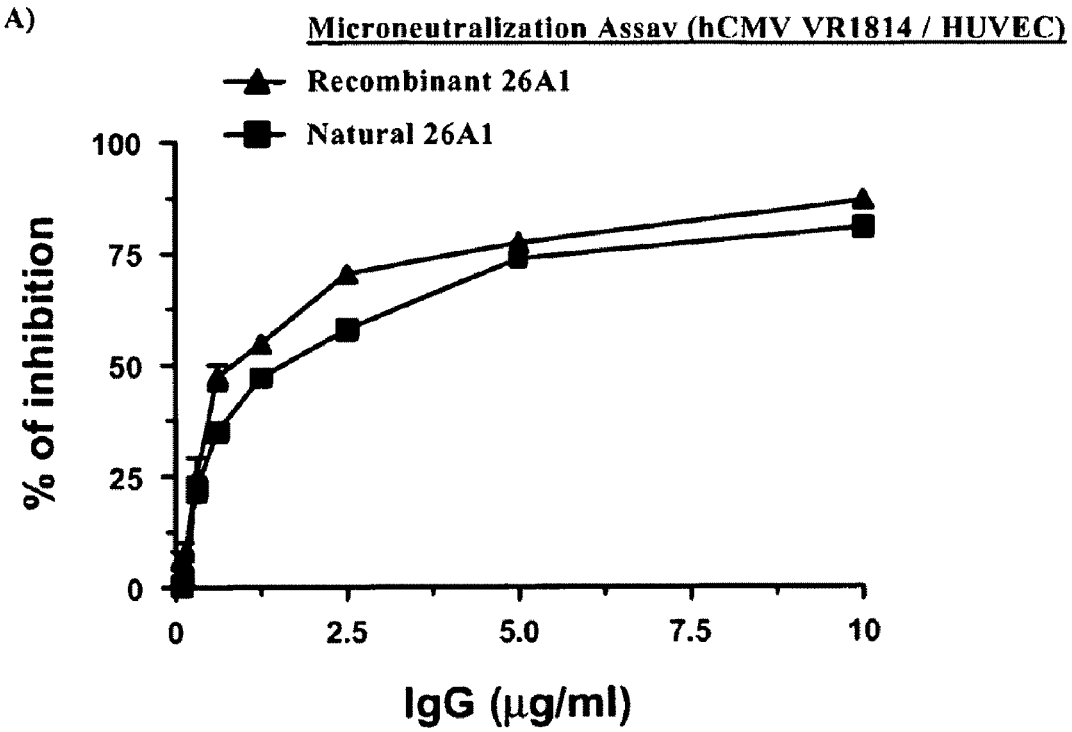
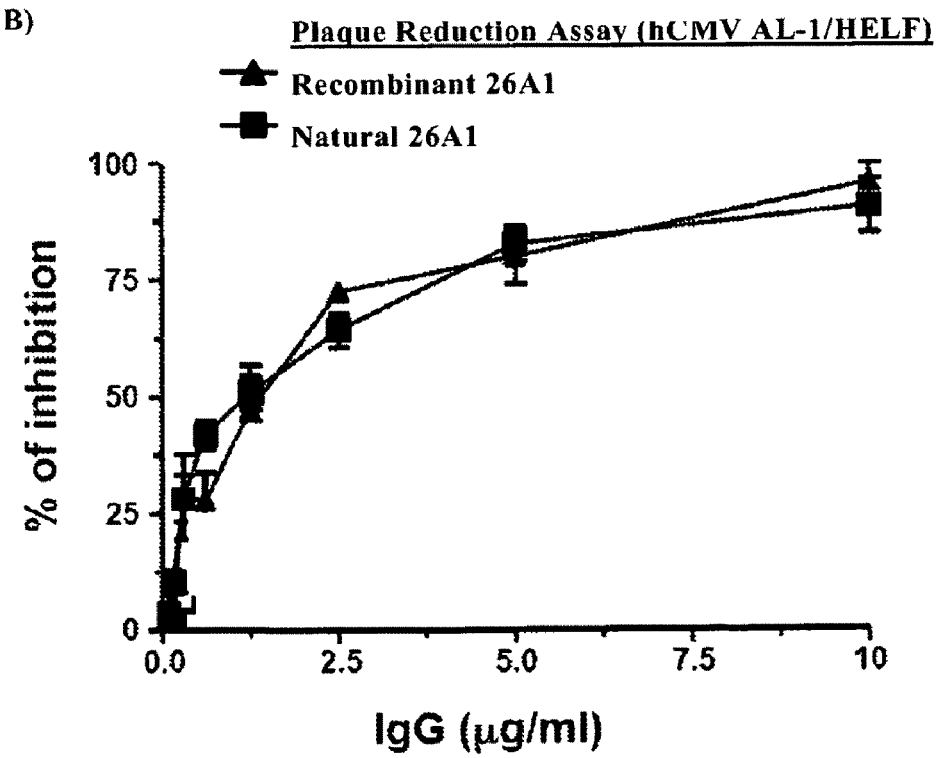

SEQUENCE LISTING

```
<160> NUMBER OF SEQ ID NOS: 17

<210> SEQ ID NO 1
<211> LENGTH: 58
<212> TYPE: PRT
<213> ORGANISM: Human cytomegalovirus

<400> SEQUENCE: 1

Ser Thr Ser His Ala Thr Ser Ser Thr His Asn Gly Ser His Thr Ser
1               5                   10                  15

Arg Thr Ser Ala Gln Thr Arg Ser Val Tyr Ser Gln His Val Thr
            20                  25                  30

Ser Ser Glu Ala Val Ser His Arg Ala Asn Glu Thr Ile Tyr Asn Thr
        35                  40                  45

Thr Leu Lys Tyr Gly Asp Val Val Gly Val
    50                  55

<210> SEQ ID NO 2
<211> LENGTH: 58
<212> TYPE: PRT
<213> ORGANISM: Human cytomegalovirus
```

<400> SEQUENCE: 2

Ser Thr Arg Gly Thr Ser Ala Thr His Ser His His Ser His Thr
1               5                   10                  15

Thr Ser Ala Ala His Ser Arg Ser Gly Ser Val Ser Gln Arg Val Thr
            20                  25                  30

Ser Ser Gln Thr Val Ser His Gly Val Asn Glu Thr Ile Tyr Asn Thr
        35                  40                  45

Thr Leu Lys Tyr Gly Asp Val Val Gly Val
    50                  55

<210> SEQ ID NO 3
<211> LENGTH: 129
<212> TYPE: PRT
<213> ORGANISM: Human cytomegalovirus

<400> SEQUENCE: 3

Leu Leu Ser His Leu Pro Ser Gln Arg Tyr Gly Ala Asp Ala Ala Ser
1               5                   10                  15

Glu Ala Leu Asp Pro His Ala Phe His Leu Leu Asn Thr Tyr Gly
            20                  25                  30

Arg Pro Ile Arg Phe Leu Arg Glu Asn Thr Thr Gln Cys Thr Tyr Asn
        35                  40                  45

Ser Ser Leu Arg Asn Ser Thr Val Val Arg Glu Asn Ala Ile Ser Phe
    50                  55                  60

Asn Phe Phe Gln Ser Tyr Asn Gln Tyr Tyr Val Phe His Met Pro Arg
65                  70                  75                  80

Cys Leu Phe Ala Gly Pro Leu Ala Glu Gln Phe Leu Asn Gln Val Asp
                85                  90                  95

Leu Thr Glu Thr Leu Glu Arg Tyr Gln Gln Arg Leu Asn Thr Tyr Ala
            100                 105                 110

Leu Val Ser Lys Asp Leu Ala Ser Tyr Arg Ser Phe Pro Gln Gln Leu
        115                 120                 125

Lys

<210> SEQ ID NO 4
<211> LENGTH: 393
<212> TYPE: DNA
<213> ORGANISM: Homo sapiens

<400> SEQUENCE: 4
caggtgcagc tgcaggagtc gggcccagga ctggtgaagc cttcacagac cctgtccctc        60
atatgcactg tctctggtgg ctccgtcagc agtggtggtg actactggac ctggatccgc       120
cagcacccag ggaagggcct ggagtggctt gggtacatcc attccagtgg gaatatcttc       180
tacaacccgt ccctcaagag tcgactgacc ttatcaatgg acacgtctaa gaaccaattc       240
ttcctgaagt tgacctctgt gactgccgcg gacacggccg tatattactg tgcgagagtc       300
tatcataagg attttgtagt agtaccaggt gctttcccct tgaattctg gttcgacccc        360 tggggccagg aaccctggt caccgtctcc tca                                      393

<210> SEQ ID NO 5
<211> LENGTH: 131
<212> TYPE: PRT
<213> ORGANISM: Homo sapiens

<400> SEQUENCE: 5

Gln Val Gln Leu Gln Glu Ser Gly Pro Gly Leu Val Lys Pro Ser Gln
1               5                   10                  15

Thr Leu Ser Leu Ile Cys Thr Val Ser Gly Gly Ser Val Ser Gly
            20                  25                  30

Gly Asp Tyr Trp Thr Trp Ile Arg Gln His Pro Gly Lys Gly Leu Glu
        35                  40                  45

Trp Leu Gly Tyr Ile His Ser Ser Gly Asn Ile Phe Tyr Asn Pro Ser
50                  55                  60

Leu Lys Ser Arg Leu Thr Leu Ser Met Asp Thr Ser Lys Asn Gln Phe
65                  70                  75                  80

Phe Leu Lys Leu Thr Ser Val Thr Ala Ala Asp Thr Ala Val Tyr Tyr
                85                  90                  95

Cys Ala Arg Val Tyr His Lys Asp Phe Val Val Pro Gly Ala Phe
            100                 105                 110

Pro Phe Glu Phe Trp Phe Asp Pro Trp Gly Gln Gly Thr Leu Val Thr
            115                 120                 125

Val Ser Ser
    130

<210> SEQ ID NO 6
<211> LENGTH: 10
<212> TYPE: PRT
<213> ORGANISM: Homo sapiens

<400> SEQUENCE: 6

Gly Gly Ser Val Ser Ser Gly Gly Asp Tyr
1               5                   10

<210> SEQ ID NO 7
<211> LENGTH: 7
<212> TYPE: PRT
<213> ORGANISM: Homo sapiens

<400> SEQUENCE: 7

Ile His Ser Ser Gly Asn Ile
1               5

<210> SEQ ID NO 8
<211> LENGTH: 23
<212> TYPE: PRT
<213> ORGANISM: Homo sapiens

<400> SEQUENCE: 8

Ala Arg Val Tyr His Lys Asp Phe Val Val Pro Gly Ala Phe Pro
1               5                   10                  15

Phe Glu Phe Trp Phe Asp Pro
            20

<210> SEQ ID NO 9
<211> LENGTH: 330
<212> TYPE: DNA
<213> ORGANISM: Homo sapiens

<400> SEQUENCE: 9
tcctatgtgc tgactcagcc accctcggtg tcagtggccc caggacagac ggccaggatt    60
gccctgcggg ggaacgagat tggaagtaag agtgtccact ggtaccagca gaagccaggc   120
caggcccctg tgctggtcgt ccatgatgac agcgaccggc cctcagggat ccctgaccga   180
ttctctggct ccaactctgg gaacacggcc accctgacca tcagcagggt cgaagccggg   240
gatgaggccg actattactg tcaggtgtgg gatagtggta gtgatcatca tgtggtattc   300
ggcggaggga ccaagctgac cgtcctaggt                                     330

<210> SEQ ID NO 10
<211> LENGTH: 110
<212> TYPE: PRT
<213> ORGANISM: Homo sapiens

<400> SEQUENCE: 10

Ser Tyr Val Leu Thr Gln Pro Pro Ser Val Ser Val Ala Pro Gly Gln
1               5                   10                  15
Thr Ala Arg Ile Pro Cys Gly Gly Asn Glu Ile Gly Ser Lys Ser Val
            20                  25                  30
His Trp Tyr Gln Gln Lys Pro Gly Gln Ala Pro Val Leu Val Val His
        35                  40                  45
Asp Asp Ser Asp Arg Pro Ser Gly Ile Pro Asp Arg Phe Ser Gly Ser
    50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Asp Ser Gly Ser Asp His
                85                  90                  95
His Val Val Phe Gly Gly Gly Thr Lys Leu Thr Val Leu Gly
            100                 105                 110

<210> SEQ ID NO 11
<211> LENGTH: 6
<212> TYPE: PRT
<213> ORGANISM: Homo sapiens

<400> SEQUENCE: 11

Glu Ile Gly Ser Lys Ser
1               5

<210> SEQ ID NO 12
<211> LENGTH: 3
<212> TYPE: PRT
<213> ORGANISM: Homo sapiens

<400> SEQUENCE: 12

Asp Asp Ser
1

<210> SEQ ID NO 13
<211> LENGTH: 12
<212> TYPE: PRT
<213> ORGANISM: Homo sapiens

<400> SEQUENCE: 13

Gln Val Trp Asp Ser Gly Ser Asp His His Val Val
1               5                   10

<210> SEQ ID NO 14
<211> LENGTH: 1449
<212> TYPE: DNA
<213> ORGANISM: Artificial
<220> FEATURE:
<223> OTHER INFORMATION: Recombinant 26A1 IgG1 Heavy Chain

<400> SEQUENCE: 14
atgaacatac tgtggagcat gctcctgctg gtggcagctc ccagatgggt cctgtcccag      60
gtgcagctgc aggagtcggg cccaggactg gtgaagcctt cacagaccct gtccctcata    120
tgcactgtct ctggtggctc cgtcagcagt ggtggtgact actggacctg gatccgccag    180
cacccaggga agggcctgga gtggcttggg tacatccatt ccagtgggaa tatcttctac    240

```
aacccgtccc tcaagagtcg actgaccttn tcaatggaca cgtctaagaa ccaattcttc    300
ctgaagttga cctctgtgac tgccgcggac acggccgtat attactgtgc gagagtctat    360
cataaggatt ttgtagtagt accaggtgct ttccccttttg aattctggtt cgacccctgg   420
ggccagggaa ccctggtcac cgtctcctca ggatccgcct ccaccaaggg cccatcggtc    480
ttccccctgg cacctcctc caagagcacc tctgggggca cagcggccct gggctgcctg     540
gtcaaggact acttccccga accggtgacg gtgtcgtgga actcaggcgc cctgaccagc    600
ggcgtgcaca ccttcccggc tgtcctacag tcctcaggac tctactccct cagcagcgtg    660
gtgaccgtgc cctccagcag cttgggcacc cagacctaca tctgcaacgt gaatcacaag    720
cccagcaaca ccaaggtgga caagaaagtt gagcccaaat cttgtgacaa aactcacaca    780
tgcccaccgt gcccagcacc tgaactcctg ggggaccgt cagtcttcct cttccccca      840 aaacccaagg acaccctcat gatctcccgg acccctgagg tcacatgcgt ggtggtggac    900
gtgagccacg aagaccctga ggtcaagttc aactggtacg tggacggcgt ggaggtgcat    960
aatgccaaga caaagccgcg ggaggagcag tacaacagca cgtaccgggt ggtcagcgtc    1020
ctcaccgtcc tgcaccagga ctggctgaat ggcaaggagt acaagtgcaa ggtctccaac    1080
aaagccctcc cagcccccat cgagaaaacc atctccaaag ccaaagggca gccccgagaa    1140
ccacaggtgt acaccctgcc cccatcccgg gatgagctga ccaagaacca ggtcagcctg    1200
acctgcctgg tcaaaggctt ctatcccagc gacatcgccg tggagtggga gagcaatggg    1260
cagccggaga acaactacaa gaccacgcct cccgtgctgg actccgacgg ctccttcttc    1320
ctctacagca agctcaccgt ggacaagagc aggtggcagc aggggaacgt cttctcatgc    1380
tccgtgatgc atgaggctct gcacaaccac tacacgcaga gagcctctc cctgtctccg     1440 ggtaaatga                                                            1449
```

<210> SEQ ID NO 15
<211> LENGTH: 482
<212> TYPE: PRT
<213> ORGANISM: Artificial
<220> FEATURE:
<223> OTHER INFORMATION: Recombinant 26A1 IgG1 Heavy Chain

<400> SEQUENCE: 15

```
Met Asn Ile Leu Trp Ser Met Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Gln Thr Leu Ser Leu Ile Cys Thr Val Ser Gly Gly Ser Val
        35                  40                  45

Ser Ser Gly Gly Asp Tyr Trp Thr Trp Ile Arg Gln His Pro Gly Lys
    50                  55                  60

Gly Leu Glu Trp Leu Gly Tyr Ile His Ser Ser Gly Asn Ile Phe Tyr
65                  70                  75                  80

Asn Pro Ser Leu Lys Ser Arg Leu Thr Leu Ser Met Asp Thr Ser Lys
                85                  90                  95

Asn Gln Phe Phe Leu Lys Leu Thr Ser Val Thr Ala Ala Asp Thr Ala
            100                 105                 110

Val Tyr Tyr Cys Ala Arg Val Tyr His Lys Asp Phe Val Val Val Pro
        115                 120                 125

Gly Ala Phe Pro Phe Glu Phe Trp Phe Asp Pro Trp Gly Gln Gly Thr
    130                 135                 140
```

```
Leu Val Thr Val Ser Ser Gly Ser Ala Ser Thr Lys Gly Pro Ser Val
145                 150                 155                 160

Phe Pro Leu Ala Pro Ser Ser Lys Ser Thr Ser Gly Gly Thr Ala Ala
            165                 170                 175

Leu Gly Cys Leu Val Lys Asp Tyr Phe Pro Glu Pro Val Thr Val Ser
        180                 185                 190

Trp Asn Ser Gly Ala Leu Thr Ser Gly Val His Thr Phe Pro Ala Val
    195                 200                 205

Leu Gln Ser Ser Gly Leu Tyr Ser Leu Ser Ser Val Val Thr Val Pro
210                 215                 220

Ser Ser Ser Leu Gly Thr Gln Thr Tyr Ile Cys Asn Val Asn His Lys
225                 230                 235                 240

Pro Ser Asn Thr Lys Val Asp Lys Lys Val Glu Pro Lys Ser Cys Asp
            245                 250                 255

Lys Thr His Thr Cys Pro Pro Cys Pro Ala Pro Glu Leu Leu Gly Gly
        260                 265                 270

Pro Ser Val Phe Leu Phe Pro Pro Lys Pro Lys Asp Thr Leu Met Ile
    275                 280                 285

Ser Arg Thr Pro Glu Val Thr Cys Val Val Val Asp Val Ser His Glu
290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
            325                 330                 335

Val Val Ser Val Leu Thr Val Leu His Gln Asp Trp Leu Asn Gly Lys
        340                 345                 350

Glu Tyr Lys Cys Lys Val Ser Asn Lys Ala Leu Pro Ala Pro Ile Glu
    355                 360                 365

Lys Thr Ile Ser Lys Ala Lys Gly Gln Pro Arg Glu Pro Gln Val Tyr
370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
            405                 410                 415

Glu Ser Asn Gly Gln Pro Glu Asn Asn Tyr Lys Thr Thr Pro Pro Val
        420                 425                 430

Leu Asp Ser Asp Gly Ser Phe Phe Leu Tyr Ser Lys Leu Thr Val Asp
    435                 440                 445

Lys Ser Arg Trp Gln Gln Gly Asn Val Phe Ser Cys Ser Val Met His
450                 455                 460

Glu Ala Leu His Asn His Tyr Thr Gln Lys Ser Leu Ser Leu Ser Pro
465                 470                 475                 480

Gly Lys

<210> SEQ ID NO 16
<211> LENGTH: 705
<212> TYPE: DNA
<213> ORGANISM: Artificial
<220> FEATURE:
<223> OTHER INFORMATION: Recombinant 26A1 IgG1 Light Chain

<400> SEQUENCE: 16
atggcctgga ccgttctcct cctcggcctc ctctctcact gcacaggttc tgtgacctcc    60
tatgtgctga ctcagccacc ctcggtgtca gtggccccag acagacggc caggattccc    120 tgtgggggga acgagattgg aagtaagagt gtccactggt accagcagaa gccaggccag    180
```

```
gcccctgtgc tggtcgtcca tgatgacagc gaccggccct cagggatccc tgaccgattc    240
tctggctcca actctgggaa cacggccacc ctgaccatca gcagggtcga agccggggat    300
gaggccgact attactgtca ggtgtgggat agtggtagtg atcatcatgt ggtattcggc    360
ggagggacca agctgaccgt cctaggtcag cccaaggctg cccctcggt cactctgttc      420 ccgcccctcct ctgaggagct tcaagccaac aaggccacac tggtgtgtct cataagtgac   480
ttctacccgg gagccgtgac agtggcctgg aaggcagata gcagccccgt caaggcggga   540
gtggagacca ccacaccctc caaacaaagc aacaacaagt acgcggccag cagctatctg    600
agcctgacgc ctgagcagtg gaagtcccac agaagctaca gctgccaggt cacgcatgaa    660
gggagcaccg tggagaagac agtggcccct acagaatgtt catag                    705
```

```
<210> SEQ ID NO 17
<211> LENGTH: 234
<212> TYPE: PRT
<213> ORGANISM: Artificial
<220> FEATURE:
<223> OTHER INFORMATION: Recombinant 26A1 IgG1 Light Chain

<400> SEQUENCE: 17

Met Ala Trp Thr Val Leu Leu Gly Leu Leu Ser His Cys Thr Gly
1               5                   10                  15

Ser Val Thr Ser Tyr Val Leu Thr Gln Pro Pro Ser Val Ser Val Ala
            20                  25                  30

Pro Gly Gln Thr Ala Arg Ile Pro Cys Gly Gly Asn Glu Ile Gly Ser
        35                  40                  45

Lys Ser Val His Trp Tyr Gln Gln Lys Pro Gly Gln Ala Pro Val Leu
    50                  55                  60

Val Val His Asp Asp Ser Asp Arg Pro Ser Gly Ile Pro Asp Arg Phe
65                  70                  75                  80

Ser Gly Ser Asn Ser Gly Asn Thr Ala Thr Leu Thr Ile Ser Arg Val
                85                  90                  95

Glu Ala Gly Asp Glu Ala Asp Tyr Tyr Cys Gln Val Trp Asp Ser Gly
            100                 105                 110

Ser Asp His His Val Val Phe Gly Gly Gly Thr Lys Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

ANTIBODIES AGAINST HUMAN CYTIMEGALOVIRUS (HCMV)

CROSS-REFERENCE TO RELATED APPLICATIONS

This is the U.S. national phase application of PCT/EP2007/064094, filed Dec. 17, 2007, which claims the benefit of PCT/EP2006/069780, filed Dec. 15, 2006 and European patent application No. 07110693.4, filed Jun. 20, 2007.

TECHNICAL FIELD

The invention relates to novel antibody sequences isolated from human B cells having biological activities specific for a virus that infects human cells.

BACKGROUND OF THE INVENTION

Human Cytomegalovirus (hCMV) is a widespread, highly species-specific herpesvirus, causing significant morbidity and mortality in immunosuppressed or immunologically immature individuals.

Several recent reviews analyze hCMV biology and clinical manifestations (Landolfo S et al., 2003; Gandhi M and Khanna R, 2004; Soderberg-Naucler C, 2006a). This viral pathogen infects the majority of the population worldwide and is acquired in childhood, following the contact with a bodily fluid, since the virus enters through endothelial cells and epithelial cells of the upper alimentary or respiratory systems, or through the genitourinary system. Seropositivity to hCMV is more prevalent in underdeveloped countries or in geographical areas with lower income.

Following a primary infection, hCMV can persist in specific host cells of the myeloid lineage in a latent state, replicating and disseminating in many different cell types (haematopoietic cells, epithelial cells, endothelial cells, or fibroblasts) and escaping the host immune system. The hCMV infection is generally asymptomatic in healthy people since hCMV infection and dissemination is maintained under control by the immune system, but total hCMV clearance is rarely achieved. In fact, hCMV virus has developed efficient mechanisms that allow viral genome to remain in selected sites in a latent state.

Any situation that weakens immune functions, such as stress conditions or specific medical treatments, can lead to hCMV reactivation. Clinical manifestations of hCMV (such as retinitis, enterocolitis, pneumonitis, gastritis, or hepatitis) can occur following viral primary infection, reinfection, or reactivation. About 10% of infants are infected by the age of 6 months following transmission from their mothers via the placenta, during delivery, or by breastfeeding.

The hCMV virion consists of an icosahedral nucleocapsid which contains a linear, 230 kb-long, double-stranded DNA genome. The expression of hCMV genome is controlled by a complex cascade of transcriptional events that leads to the synthesis of more than 200 proteins involved in a large variety of biological activities involved in viral infection, latency, and replication (Britt W and Mach M, 1996).

The structural proteins form the virion envelope that is extremely complex and still incompletely defined. It includes glycoproteins that are homologues of structural proteins identified in other herpesviridae and that can form disulfide-linked protein complexes within the virion : gCI (including only gB), gCII (including gM and gN) and gCIII (including gH, gL and gO). The gB, gH, and gN genes have been also used for genotyping hCMV strains (Coaquette A et al.,2004; Dar L, 2007).

The glycoproteins gN and gM are the most abundant and, together with gH and gB, have been shown to be essential for the initial interaction between the hCMV envelope and host cell surface, and consequently for the production of infectious hCMV. For this reason, compounds targeting gB, gH, gN, and/or gM can efficiently inhibit hCMV infection by blocking the entry of circulating hCMV virions into the cells, following hCMV infection, reinfection, or reactivation.

Treatment of hCMV infections is difficult because there are few therapeutic options available. The presently available drugs compounds that inhibit viral replication (Ganciclovir, Cidofivir, Foscarnet, Maribavir and others drugs under development) produce a significant clinical improvement, but may suffer from poor oral bioavailability, low potency, the emergence of hCMV resistance (due to mutations in the viral targets), and dose-limiting toxicities (De Clercq E, 2003; Baldanti F and Gerna G, 2003; Gilbert C and Boivin G, 2005).

Novel means for preventing and treating hCMV infection are needed, especially for immunocompromised individuals, in transplantation settings, and in prenatal prevention. In fact, hCMV is a clinically important opportunistic pathogen in HIV patients and in organ transplant recipients, where it contributes to graft loss independently from graft rejection, resulting in morbidity and mortality (Puius Y and Snydman D, 2007). The increasing number of bone marrow and solid organ-transplant recipients raises the likelihood of hCMV clinical manifestations, such as hCMV retinitis (Wiegand T and Young L, 2006). Moreover, hCMV is the major infectious cause of birth defects (such as hearing loss, delayed development, or mental retardation) which are due to a congenital or perinatal hCMV infection transmitted by an hCMV-infected mother (Griffiths P and Walter S, 2005).

Thus, it is important to provide drugs for universal preemptive, prophylactic hCMV-specific treatments, for example for the prevention of hCMV disease in transplant recipients (Hebart H and Einsele H, 2004; Kalil A et al., 2005; Snydman D, 2006), in patients developing hCMV-related neuropathologies (Griffiths P, 2004) or in at risk pregnancies (Schleiss M, 2003), to prevent the vertical transmission and life-threatening hCMV infection to foetuses and neonates.

Moreover, pharmaceutical compositions against hCMV may be useful for the treatment of other, more widespread diseases (such as cardiovascular and autoimmune diseases, or some types of cancer), where hCMV is a possible cofactor and/or can be reactivated during immuniosuppressive treatments. For example, hCMV is now a human pathogen of growing importance for disorders such as long-term complications in tumour invasiveness and immune evasion since hCMV infection may have oncomodulatory effects on cell apoptosis, differentiation, and migration. In autoimmune or vascular diseases, hCMV infection may alter immune and inflammatory reactions (Cinatl J et al., 2004; Soderberg-Naucler C, 2006b).

An alternative way to prevent hCMV infection is vaccination, at the scope of providing protection in an array of high-risk patient populations. However, the correlation between vaccination and the resulting immune response is not fully understood and optimal hCMV vaccine strategy (using specific candidate antigens or live attenuated vaccines) seems depending on the patient population being targeted for protection. Therefore, prophylactic vaccination strategies are still under evaluation (McLean G et al., 2006; Schleiss M, 2005).

In view of the present limitations of pharmacological strategies for hCMV infections, the increasing knowledge of the host-hCMV relationship, and in particular on the hCMV-specific immune response, makes immune-based therapies good alternatives to substitute, or complement, existing therapies for the successful treatment of hCMV-associated complications (Gandhi M and Khanna R, 2004). Recently, a long-term protection from the lethal course of CMV infection in immunodeficient mice was achieved by transferring virus-specific memory B cells, suggesting that such cells may have a therapeutic utility (Klenovsek K et al., 2007).

An easier alternative to cell-based therapies can be passive immunotherapy, consisting in the administration to individuals of pharmaceutical compositions comprising therapeutic antibodies with a defined neutralizing activity against a human or viral antigen (e.g. hCMV).

This therapeutic approach has been designed on the antigen-binding and biological features of antibodies and antibody fragments directed against human or viral therapeutic targets (Dunman P and Nesin M, 2003; Keller M and Stiehm E, 2000). Passive immunotherapy has been introduced into clinical practice, rapidly expanding the opportunities for the treatment of a wide variety of diseases (including infectious diseases, immune-mediated diseases, and cancer). This approach can be particularly effective in patients whose immune system is unable to produce antibodies in the amounts and/or with the specificity required to block and/or eliminate the targeted molecule (Chatenoud L, 2005; Laffly E and Sodoyer R, 2005).

In the field of hCMV therapy, this approach is performed by administering intravenously human immunoglobulin preparations that are obtained by pooling human plasma with high titers of anti-hCMV antibodies, and commercialized for clinical uses (under the name of Cytotect or CytoGam). However, these products are only a partially satisfactory solution for blocking hCMV infection. In fact, this treatment is used in immunocompromised patients, mostly for pre-emptive treatment and prophylaxis where antivirals are often co-administered (Marasco W and Sui J, 2007; Nigro G et al., 2005; Bonaros N et al., 2004; Kocher A et al., 2003; Kruger R et al., 2003). Moreover, safety issues and shortage of such preparations are a growing concern, as reported in literature (Bayry J et al., 2007; Hamrock D, 2006).

Human recombinant antibodies that have high affinity for antigens expressed on hCMV envelope and are able to neutralize the infection would represent more appropriate drugs for passive immunization. In fact, several of the hCMV glycoproteins elicit strong host immune responses, including the production of virus-neutralizing antibodies, even though the stoichiometry of the envelope proteins is variable and may be altered to escape host immune response. This response is considered to be a key component of host immunity and represents a goal of both antibody and vaccine development.

Human monoclonal antibodies are the most preferable antibodies for clinical applications, due to the intrinsic limitations of murine monoclonal antibodies. However, the development of previously identified human antibodies for hCMV treatment (Matsumoto Y et al., 1986) has been interrupted since no clinical benefits were observed in studies that evaluated the efficacy of such antibodies, for example, in haematopoietic stem cell transplantation (Boeckh M et al., 2001), or in retinitis (Gilpin A et al., 2003). These failures trials warrant further studies aimed at selecting human monoclonal antibodies that more efficiently neutralize the widest variety of hCMV strains. The treatment of CMV infections would benefit from having more potent pharmaceutical compositions comprising human monoclonal antibodies that are purified from human B cells maintained in culture or produced as recombinant proteins that are expressed by human sequences introduced in mammalian cell lines.

DISCLOSURE OF THE INVENTION

The present invention provides novel antibody sequences that bind and neutralize hCMV, and that can be used for detecting, treating, inhibiting, preventing, and/or ameliorating hCMV infection or an hCMV-related disease.

Human B cells were obtained from an hCMV-seropositive individual and immortalized. This polyclonal population of immortalized, human B cells was divided for generating subcultures that were tested for the presence of antibodies (Immunoglobulins G, IgG) in the cell culture supernatant neutralizing hCMV infectivity in vitro. In particular, the type of neutralizing activity, the isotype, and the clonality were determined for the antibody secreted by the subculture named 26A1. The antibody has been affinity-purified from both the original cell culture supernant and as a recombinant human monoclonal antibody, confirming the hCMV-specific neutralizing activity using in vitro models for hCMV infection. This antibody can be used for characterizing neutralizing antigens on hCMV envelope.

The DNA sequences that encode the variable regions of the antibody secreted by the 26A1 subculture were amplified, cloned, and sequenced. The corresponding protein sequences were analyzed to identify the Complementarity Determining Regions (CDRs) that are responsible for the hCMV-specific biological activity. These sequences can be used for producing proteins having hCMV-specific binding and neutralizing properties, in the form of full antibodies, antibody fragments, or any other format of functional protein (e.g. bioactive peptide, fusion proteins) using appropriate technologies for producing recombinant proteins.

Compositions having therapeutic, prophylactic, and/or diagnostic utility in the management of hCMV infection and hCMV-related disorders can be prepared using the proteins of the invention, either as recombinant proteins or as natural antibodies purified from cell cultures originated from the 26A1 subculture. Such compositions may be used to supplement or replace present hCMV treatments based on antiviral compounds and/or intravenous immunoglobulins (IVIg) preparations.

Further embodiments of the present invention will be provided in the following Detailed Description.

DESCRIPTION OF THE FIGURES

FIG. 1: (A) Schematic representation of the CG3 antigen that has been assembled and used in a gB-specific ELISA as described in the literature (Rothe M et al., 2001). The recombinant interstrain fusion CG3 antigen corresponds to a combination of the gB Antigenic Domain 2 (AD2; SEQ ID NO : 1 and 2) from hCMV strains AD169 (SwissProt Acc. No. P06473; amino acids 27-84) and Towne (SwissProt Acc. No. P13201; amino acids 27-84). The AD2 region contains a site (amino acids 70-81, underlined) that is conserved in different viral strains and that has been shown to be recognized by neutralizing antibodies (Qadri I et al., 1992; Kropff B et al., 1993). (B) Schematic representation of the gH antigen included in the gH(Ag)-GST fusion protein used for the gH-specific ELISA assay. The recombinant antigen gH(Ag)-GST corresponds to an in-frame fusion between the gH amino terminal region (amino acids 16-144; SEQ ID NO. : 3) from the hCMV strain VR1814 (Revello M et al., 2001) and Glutathione-S-Transferase (GST). The amino terminus of gH contains a linear antibody binding site (amino acids 34-43; underlined) that is recognized by neutralizing antibodies (Urban M et al., 1992).

FIG. 4: gH(Ag)-specific (A) and CG3 antigen-specific (B) binding activity of IgG-containing supernatants from subcultures of immortalized human B cells. The ELISA was performed using the cell culture medium only (medium, negative control), or the supernatant from subcultures 26A1, 1F7 (identified in the immortalized cells obtained from CMV5 donor, as described in the patent application EP07111741), and 8C10 (identified in the immortalized cells obtained from CMV7 donor, as described in the present patent application and in patent application EP07115410). The dotted line represents the threshold value (O.D.=0.1) for considering a subculture positive.

FIG. 5: (A) Alignment of the DNA (lower case, 393 base pairs) and protein (upper case, 131 amino acids) consensus sequence of the variable region for the heavy chain of the 26A1 IgG (VH 26A1; SEQ ID NO. : 4 and 5). (B) Protein consensus sequence for VH 26A1 with the indication of predicted CDRs (HCDR1, HCDR2, and HCDR3; underlined; SEQ ID NO.: 6, 7, and 8). Alternative amino acids that were encoded by the DNA sequences cloned in plasmid from isolated E. coli transformants are indicated below the consensus protein sequence.

FIG. 6: (A) Alignment of the DNA (lower case, 330 base pairs) and protein (upper case, 110 amino acids) consensus sequence of the variable region for the light chain of the 26A1 IgG (VL 26A1; SEQ ID NO. : 9 and 10). (B) Protein consensus sequence for VL 26A1 with the indication of predicted CDRs of VL 26A1 (LCDR1, LCDR2, and LCDR3; underlined; SEQ ID NO. : 11, 12, and 13).

FIG. 7: Alignment of the DNA (lower case, 1449 base pairs; SEQ ID NO. : 14) and protein (upper case, 482 amino acids) consensus sequence of the heavy chain of recombinant human 26A1 monoclonal antibody (SEQ ID NO.: 15). The most likely cleavage site for signal peptide is between pos. 19 and 20 (VLS-QV), as determined using the SignalP 3.0 online prediction program (Bendtsen J et al., 2004). The sequence originally identified in cDNA generated from cells in 26A1 subculture is underlined (see FIG. 5). Amino acids 153-482 correspond to human IgG1 heavy chain constant region (SwissProt Acc. No. P01857).

FIG. 8: Alignment of the DNA (lower case, 705 base pairs; SEQ ID NO.: 16) and protein (upper case, 234 amino acids) consensus sequence of the light chain of recombinant human 26A1 IgG (SEQ ID NO. : 17). The most likely cleavage site for signal peptide is between pos. 16 and 17 (CTG-SV), as determined using the SignalP 3.0 online prediction program (Bendtsen J et al., 2004). The sequence originally identified in cells from 26A1 subculture is underlined (see FIG. 5). Amino acids 1-19 and 131-234 correspond to 1-19 and 131-234 of human Ig lambda chain (SwissProt Acc. No. Q8N355).

FIG. 9: hCMV-neutralizing activity of recombinant human 26A1 antibody compared to Protein A-purified natural 26A1 antibody. The activity has been tested using HELF cells and AD169 hCMV strain in a microneutralization assay (A; 1000 PFU/reaction, 72 hour post-infection) or in a plaque reduction assay (B).

FIG. 10: hCMV-neutralizing activity of recombinant human 26A1 monoclonal antibody compared to Protein A-purified natural 26A1 antibody. The activity has been tested using HUVEC human cells and VR1814 hCMV strain in a microneutralization assay (A; 1000 PFU/reaction), or using HELF human cells and AL-1 hCMV strain in a plaque reduction assay (B; 1000 PFU/reaction).

DETAILED DESCRIPTION OF THE INVENTION

Figure 2:
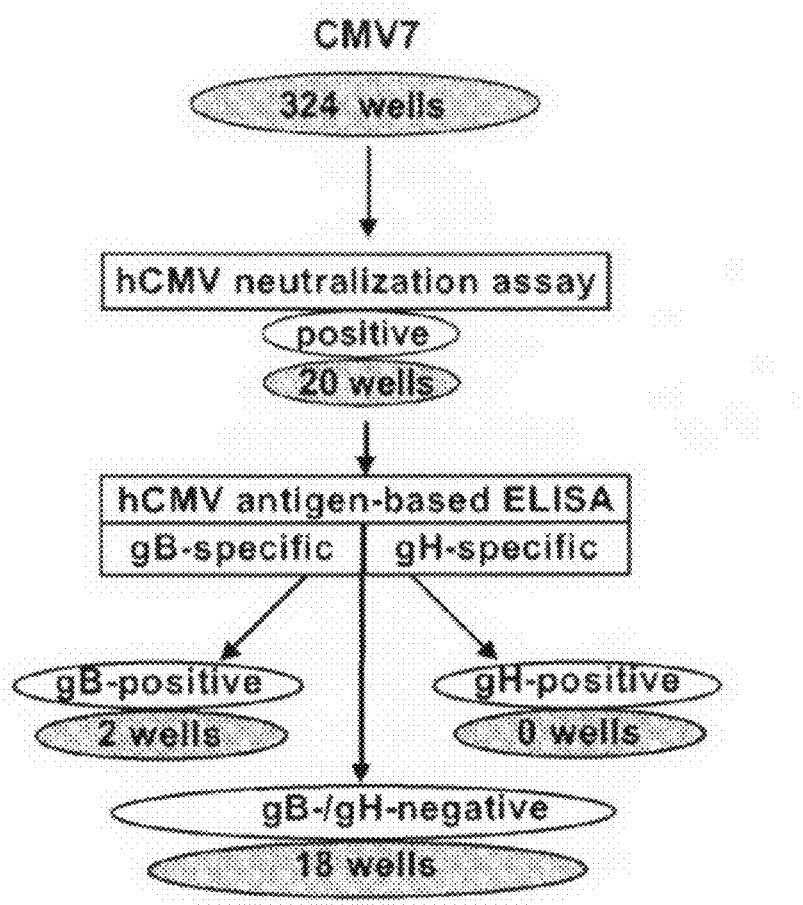
FIG. 2: overview of the selection process for identifying and characterizing subcultures (wells) that contain IgG antibodies binding and neutralizing hCMV. The subcultures were obtained by immortalizing B cells from hCMV patient (CMV7) using the EBV-based immortalization process disclosed in PCT/EP2005/056871. Supernatants from subcultures (wells) showing significant cell growth were screened directly in the hCMV microneutralization assay. Supernatants showing neutralizing activity were then screened using gB- and gH-specific ELISA. The number of positive wells for each screening assay is indicated in the grey ovals.

The methods described in PCT/EP2005/056871 allow the efficient immortalization of isotype-specific human B cells obtained from an individual, whose blood contains antibodies having biological activities (e.g. binding and/or neutralizing a human or viral target), at the scope of obtaining polyclonal populations of cells that secrete antibodies presenting such biological activities Extensive screening assays can be then performed using supernatants of subcultures obtained by these methods following a single step of cloning at low cell density (e.g. 50, 20 cells or less per well). In this manner, it is possible to obtain polyclonal populations of immortalized B cells in which a large repertoire of IgG-secreting subcultures can be characterized and consequently a number of human monoclonal IgG having the desired binding specificity for antigens and/or the biological activity can be identified.

In the present case, a polyclonal population of IgG-secreting, immortalized human B cells were obtained from the blood of an hCMV patient whose serum presented, as biological activity, a strong hCMV-neutralizing activity. The polyclonal population was used to generate, in a single subcloning step at 20 cells per well and in appropriate culture conditions, thousands of subcultures that contain immortalized human B cells. The specific biological activity was then tested in the supernatant of hundreds of efficiently growing cell cultures at the scope of selecting those presenting the stronger activity, and then determining the isotype and, if possible, the epitope of the secreted antibody.

One of the most promising subcultures, named 26A1, was used to both purify the natural human antibody from large scale cultures and to isolate the DNA encoding such antibody from the immortalized B cells. The DNA sequence was used for producing the natural human antibody as a recombinant human antibody. The natural and the recombinant human 26A1 monoclonal antibody were used for performing more extensive biological assays and for assessing their potential utility in hCMV-related clinical applications.

The examples shows how the cell culture supernatant, the natural human antibody, and the recombinant human antibody present the same biological activity determined in the original blood serum and polyclonal population of human EBV-immortalized B cells. These evidences confirm that the methods described in PCT/EP2005/056871 allow the identification, characterization, and the production of biologically active, isotype-specific, natural and recombinant human monoclonal antibodies. In fact, the complete process of cell immortalization and growth in cell culture conditions gives access to the repertoire of human antibodies in a fast, efficient and straightforward manner. Moreover, the cells resulting from the process can be frozen and screened in a different moment, or in parallel for different biological activities and/or antigens.

In one embodiment, the present invention provides proteins comprising a sequence having at least 90% identity with the sequence of the HCDR3 (CDR3 of the heavy chain variable region) of the 26A1 antibody (SEQ ID NO.: 8). Together with the HCDR1 and HCDR2 (SEQ ID NO.: 6 and SEQ ID NO.: 7), this HCDR3 is included in the variable region of the heavy chain of the 26A1 antibody (VH 26A1; FIG. 5; SEQ ID NO.: 5). This sequence is encoded by the DNA sequence (FIG. 5A; SEQ ID NO.: 4) that was amplified and cloned using cells obtained from the original subculture secreting the 26A1 antibody. Thus a protein of the invention may contain, together with the HCDR3 of the 26A1 antibody (SEQ ID NO.: 8), the sequence of the HCDR1 (SEQ ID NO.: 6) and/or HCDR2 (SEQ ID NO.: 7) of the 26A1 antibody (FIG. 5B). Such a protein may comprise a sequence having at least 90% identity with the entire sequence of the variable region of the heavy chain of the 26A1 antibody.

The 26A1 antibody also contains a variable region of a light chain for which, using the same approach, the DNA (SEQ ID NO.: 9) and the protein (SEQ ID NO.: 10) sequences, together with the specific LCDRs (SEQ ID NO.: 11, SEQ ID NO.: 12 and SEQ ID NO.: 13), have been determined (FIG. 6). Thus a protein of the Invention can further comprises one or more sequences selected from the group consisting of single LCDRs of the 26A1 antibody (SEQ ID NO.: 11, SEQ ID NO.: 12 and SEQ ID NO.: 13), which can be provided as a protein sequence comprising a sequence having at least 90% identity with VL 26A1 (FIG. 6B; SEQ ID NO.: 10). This applies in particular when a human recombinant antibody, comprising both the natural VL 26A1 and VH 26A1 sequences as light and heavy chains (in the natural conformation of a tetrameric complex comprising two light and two heavy chains, or in a single protein as recombinant variant of the natural antibody), is desired.

Wherever a level of identity is indicated, this level of identity should be determined on the full length of the relevant sequence of the invention.

The HCDR3 of the 26A1 antibody can be considered as characterizing the antigen-binding portion of a specific human antibody that is capable of binding and neutralizing hCMV, as shown in the Examples. Even though, several or all CDRs of an antibody are generally required for obtaining an antigen-binding surface, HCDR3 is the CDR showing the highest differences between antibodies not only with respect to sequence but also with respect to length. Such diversities are fundamental components of binding regions for the recognition of essentially any antigen by the humoral immune system (Xu and Davis, 2000; Barrios Y et al. 2004; Bond C et al., 2003). Alternatively, combinations of CDRs can be linked to each other in very short proteins that retain the original binding properties, as recently reviewed (Ladner R, 2007).

Thus, hCMV-neutralizing proteins can be generated using the HCDR3 of 26A1 antibody as hCMV binding moiety, in combination or not with other CDRs from the 26A1 antibody, which can be expressed within an antibody protein framework (Knappik A et al., 2000), or within a protein framework unrelated to antibodies (Kiss C et al., 2006).

The variable region of the heavy and light chains forming 26A1 antibody (or selected portions, such as the isolated HCDRs and LCDRs) can be included in any other protein format for functional antibody fragments, as described in the literature under different names such as Scfv (single-chain fragment variable), Fab (variable heavy/light chain heterodimer), diabody, peptabody, VHH (variable domain of heavy chain antibody), isolated heavy or light chains, bispecific antibodies, and other engineered antibody variants for non-/clinical applications (Jain M et al., 2007; Laffly E and Sodoyer R, 2005).

Alternative antibodies can be generated using the sequences of 26A1 antibody through a process of light-chain variable domain (VL) shuffling. In fact, several different antibodies can be generated and tested for hCMV-specific activity using a single heavy chain variable domain VH (such as the one of 26A1) combined with a library of VL domains, at the scope of determining VH/VL combinations with improved properties in terms of affinity, stability, and/or recombinant production (Ohlin M et al., 1996; Rojas G et al., 2004; Watkins N et al., 2004).

Novel approaches for developing new bioactive peptides also showed the feasibility of synthesizing CDR-derived peptides that contain L-amino acids and/or D-amino acids, that maintain the original activity, and that may have a more appropriate pharmacological profile (Smith J et al., 1995; Levi M et al., 2000; Wijkhuisen A et al., 2003).

Thus, the HCDR3 of the 26A1 antibody as well as sequences highly similar to HCDR3 of 26A1 antibody, fusion proteins containing it, and synthetic peptides derived from them (e.g. containing L-amino acids, D-amino acids, in the normal or in the retro-inverso conformation), can be tested and used as hCMV-binding and neutralizing proteins.

Moreover, it is known that antibodies may be modified in specific positions in order to have antibodies with improved features, in particular for clinical applications (such as better pharmacokinetic profile or higher affinity for an antigen). These changes can be made in the CDRs and/or framework of the 26A1 antibody and the sequence can be chosen by applying any of the dedicated technologies for the rational design of antibodies that make use of affinity maturation and other processes (Kim S et al., 2005; Jain M et al., 2007).

The proteins of the invention may be provided as antibodies in general, such as fully human monoclonal antibodies having a specific isotype. The IgG isotype, for example, is the antibody format of almost all approved therapeutic antibodies (Laffly E and Sodoyer R, 2005). However, antigen binding portions isolated from a HIV-neutralizing IgG1 were transferred on a human IgA sequence and the resulting antibody is capable of inhibiting HIV infection as well (Mantis N et al., 2007).

The protein of the invention may be also provided as antibody fragments, bioactive peptides, or fusion proteins. All these alternative molecules should maintain, if not enhance, the original hCMV binding and neutralization properties that were determined for the 26A1 antibody. In the case of fusion proteins, the heterologous protein sequences can be located in the N- or C-terminal position to the 26A1-derived sequence, without affecting the correct expression and biological activity of the hCMV-specific moiety (e.g. an antibody fragment).

The term "heterologous protein sequence" indicates a protein sequence that is not naturally present in the N- or C-terminal position to the hCMV-specific moiety (e.g. an antibody fragment). The DNA sequence encoding this protein sequence is generally fused by recombinant DNA technologies and comprises a sequence encoding at least 5 amino acids.

Such a heterologous protein sequence is generally chosen for providing additional properties to the hCMV-specific antibody fragment for specific diagnostic and/or therapeutic uses.

Examples of such additional properties include: better means for detection or purification, additional binding moieties or biological ligands, or post-translational modification of a fusion protein (e.g. phosphorylation, glycosylation, ubiquitination, SUMOylation, or endoproteolytic cleavage).

Alternatively (or additionally to the fusion with a heterologous protein sequence), the activity of a protein of the invention may be improved with the conjugation to different compound such as therapeutic, stabilizing, or diagnostic agents. Examples of these agents are detectable labels (e.g. a radioisotope, a fluorescent compound, a toxin, a metal atom, a chemiluminescent compound, a bioluminescent compound, or an enzyme) that can be bound using chemical linkers or polymers. The hCMV-specific biological activity may be improved by the fusion with another therapeutic protein, such as a protein or a polymer altering the metabolism and/or the stability in diagnostic or therapeutic applications.

Means for choosing and designing protein moieties, ligands, and appropriate linkers, as well as methods and strategies for the construction, purification, detection and use of fusion proteins are provided in the literature (Nilsson J et al., 1997; "Applications Of Chimeric Genes And Hybrid Proteins" Methods Enzymol. Vol. 326-328, Academic Press, 2000; WO 01/77137) and are commonly available in clinical and research laboratories. For example, the fusion protein may contain sequences recognized by commercial antibodies (including tags such as polyhistidine, FLAG, c-Myc, or HA tags) that can facilitate the in vivo and/or in vitro identification of the fusion protein, or its purification.

Other protein sequences can be identified by direct fluorescence analysis (as in the case of Green Fluorescent Protein), or by specific substrates or enzymes (e.g. using proteolytic sites). The stability of hCMV-specific antibodies, antibody fragments, bioactive peptides, and fusion proteins may be improved with the fusion with a carrier protein, such as phage coat protein (cp3 or cp8), Maltose Binding Protein (MBP), Bovine Serum Albumin (BSA), or Glutathione-S-Transferase (GST).

The 26A1 antibody is a main object of the invention and it has been characterized, within the supernatant of a specific subculture, as a human IgG1 monoclonal antibody which has been selected due to the capability of neutralizing hCMV. This property have been determined by in vitro neutralization assays using cell culture supernatant (Table 1), and later as a Protein A-purified (FIG. 3) and recombinant (FIGS. 9 and 10; SEQ ID NO.: 15 and 17) human monoclonal antibody.

The specific hCMV antigen that is recognized by 26A1 antibody has not been determined using a panel of known hCMV neutralizing epitopes in viral antigens (see FIGS. 1, 2, and 4). Consequently, this IgG antibody can be used for defining an hCMV-neutralizing epitope and proteins binding such antigen (e.g. in form of the antibodies, antibody fragments, bioactive peptides, fusion protein, or any natural/recombinant proteins) that should be capable of neutralizing hCMV infection by recognizing such epitope.

In the past, ELISA or Western Blot using hCMV-specific truncated proteins or synthetic peptides have been also used (Greijer A et al., 1999; Ohlin M et al., 1993) and in this way antibodies directed to hCMV have been defined according to their antigen, being glycoprotein H (WO 94/16730, WO 94/09136, WO 92/11018), glycoprotein B (EP248909, WO 93/21952) or glycoprotein M/glycoprotein N (Shimamura M et al., 2006). Moreover, other components of the hCMV virion not only affect viral tropism but can be targets of hCMV neutralizing antibodies, as in the case of pUL130 and pUL128 (Wang D and Shenk T, 2005). Thus, the CMV antigen/epitope recognized by the 26A1 antibodies can be identified by different in vitro assays based on the literature cited above A further embodiment of the present invention is human IgG1 antibody secreted by the 26A1 subculture, which can be provided as a Protein A-purified natural antibody that binds and neutralized hCMV. This IgG1 antibody can be used for identifying competing proteins that can bind and neutralize hCMV as well. Similar proteins are provided in the above description and in the Examples, in particular as recombinant human antibodies and antibody fragments.

The mechanism of hCMV neutralization, that are associated to the viral epitope recognized by the 26A1 antibody and the other proteins defined above, can be characterized using the available assays for specific structural hCMV proteins and/or strain, as shown in the literature using panels of human sera (Navarro D et al., 1997; Klein M et al., 1999; Weber B et al., 1993; Rasmussen L et al., 1991; Marshall G et al., 2000) or of monoclonal antibodies (Schoppel K et al., 1996; Simpson J et al., 1993; Gicklhorn D et al., 2003).

Further objects of the inventions are the nucleic acids encoding any of the antibodies, antibody fragments, fusion proteins, bioactive peptides, or isolated HCDRs and LCDRs defined above. The examples provide such sequences in particular as encoding the full variable regions of the 26A1 heavy (SEQ ID NO.: 4) and light (SEQ ID NO.: 9) chains (FIGS. 5A and 6A). These DNA sequences (or selected portions, such as those encoding the specific HCDRs and LCDRs; FIGS. 5 and 6) can be transferred in vectors for expressing them in one of the alternative formats for antibodies (e.g. full, affinity-matured, or CDR-grafted or antibody fragments) or fusion proteins. These nucleic acids can comprise a sequence having at least 90% identity with SEQ ID NO.: 4, with or without a sequence further comprising a sequence having at least 90% identity with SEQ ID NO.: 9, depending on whether sequences from only the heavy chain of 26A1 or both heavy and light chain are needed.

When a fully human antibody is desirable, the antibody should further comprise a heavy chain constant region selected from the group consisting of IgG1, IgG2, IgG3, IgG4, IgM, IgA and IgE constant regions. Preferably, the heavy chain constant region is a human IgA, IgG1 (as in the natural 26A1 antibody characterized from the 26A1 subculture), IgG2, or IgG4. The nucleic acid sequences encoding the full variable regions of 26A1 heavy and light chains have been cloned and characterized by means of PCR reactions and vectors containing the resulting PCR products, which have used for transforming E. coli cells. Such sequences can be transferred (in part or in their entirety) into another vector, in particular in the expression cassette of a vector or of distinct vectors where they are operably linked to appropriate regulatory sequences (e.g. promoters, transcription terminators).

The human 26A1 monoclonal antibody, or any other protein sequences derived from such antibody, can be expressed as a recombinant protein using such vectors for transforming the appropriate host cells. The host cells comprising the nucleic acids of the invention can be prokaryotic or eukaryotic host cells and should allow the secretion of the desired recombinant protein. Methods for producing such proteins include culturing host cells transformed with the expression vectors comprising their coding sequences under conditions suitable for protein expression and recovering the protein from the host cell culture. The vectors should include a promoter, a ribosome binding site (if needed), the start/stop codons, and the leader/secretion sequence, that can drive the expression of a mono or bicistronic transcript for the desired protein. The vectors should allow the expression of the recombinant protein in the prokaryotic or eukaryotic host cells. A cell line substantially enriched in such cells can be then isolated to provide a stable cell line.

The nucleic acids and host cells can be used for producing a protein of the invention by applying common recombinant DNA technologies. Briefly, the desired DNA sequences can be either extracted by digesting the initial cloning vector with restriction enzymes, or amplified using such a vector as a template for a Polymerase Chain Reaction (PCR) and the PCR primers for specifically amplifying full variable regions of the heavy and light chains or only portions of them (e.g. the HCDR3 sequence). These DNA fragments can be then transferred into more appropriate vectors for the expression into prokaryotic or eukaryotic host cells, as described in books and reviews on how to clone and produce recombinant proteins, including titles in the series "A Practical Approach" published by Oxford Univ. Press ("DNA Cloning 2: Expression Systems", 1995; "DNA Cloning 4: Mammalian Systems", 1996; "Protein Expression", 1999; "Protein Purification Techniques", 2001).

For eukaryotic hosts (e.g. yeasts, insect or mammalian cells), different transcriptional and translational regulatory sequences may be employed, depending on the nature of the host. They may be derived from viral sources, such as adenovirus, bovine Papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for the transient (or constitutive) repression and activation and for modulating gene expression.

The sequence encoding the recombinant protein can be adapted and recloned for making modifications at the DNA level only that can be determined, for example, using software for selecting the DNA sequence in which the codon usage and the restriction sites are the most appropriate for cloning and expressing a recombinant protein in specific vectors and host cells (Grote A et al., 2005; Carton J et al., 2007).

During further cloning steps, protein sequences can be added in connection to the desired antibody format (Scfv, Fab, antibody fragment, fully human antibody, etc.), or to the insertion, substitution, or elimination of one or more internal amino acids. These technologies can also be used for further structural and functional characterization and optimization of the therapeutic properties of proteins in general, and of antibodies in particular (Kim S et al., 2005), or for generating vectors allowing their stable in vivo delivery (Fang J et al., 2005). For example, recombinant antibodies can also be modified at the level of structure and/or activity by choosing a specific Fc region to be fused to the variable regions (Furebring C et al., 2002; Logtenberg T, 2007), by generating single chain antibody fragments (Gilliland L et al., 1996), and by adding stabilizing peptide sequences, (WO 01/49713), polymers or radiochemicals to chemically modified residues (Chapman A et al., 1999).

The DNA sequence coding for the recombinant protein, once inserted into a suitable episomal or non-homologously or homologously integrating vector, can be introduced in the appropriate host cells by any suitable means (transformation, transfection, conjugation, protoplast fusion, electroporation, calcium phosphate precipitation, direct microinjection, etc.) to transform them. Important factors to be considered when selecting a particular vector include: the ease with which host cells that contain the vector may be recognized and selected; the number of copies of the vector which are desired; and whether the vector is able to "shuttle" between host cells of different species.

The cells which have been stably transformed by the introduced DNA can be selected by also introducing one or more markers which allow for selection of host cells which contain the expression vector. The marker may also provide for phototrophy to an auxotropic host, biocide resistance, e.g. antibiotics, or heavy metals such as copper, or the like, and may be cleavable or repressed if needed. The selectable marker gene can either be directly linked to the DNA gene sequences to be expressed, or introduced into the same cell by co-transfection. Additional transcriptional regulatory elements may also be needed for optimal expression.

Host cells may be either prokaryotic or eukaryotic. Amongst prokaryotic host cells, the preferred ones are *B. subtilis* and *E. coli*. Amongst eukaryotic host cells, the preferred ones are yeast, insect, or mammalian cells. In particular, cells such as human, monkey, mouse, insect (using baculovirus-based expression systems) and Chinese Hamster Ovary (CHO) cells (as shown in the Examples), provide post-translational modifications to protein molecules, including correct folding or certain forms of glycosylation at correct sites. Also yeast cells can carry out post-translational peptide modifications including glycosylation. A number of recombinant DNA strategies exist which utilize strong promoter sequences and high copy number of plasmids that can be utilized for production of the desired proteins in yeast. Yeast recognizes leader sequences in cloned mammalian gene products and secretes peptides bearing leader sequences (i.e., pre-peptides).

Mammalian cell lines available as hosts for expression are known in the art and include many immortalized cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Per.C6, Bowes melanoma and human hepatocellular carcinoma (for example Hep G2) cells and a number of other cell lines. In the baculovirus system, the materials for baculovirus/insect cell expression systems are commercially available in kit form (e.g. commercialized by Invitrogen).

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for one or more days in an enriched media before they are switched to selective media. The purpose of the selectable marker is to confer resistance to selection, and its presence allows growth and recovery of cells that successfully express the introduced sequences. Resistant clones of stably transformed cells may proliferate using tissue culture techniques appropriate to the cell type. A cell line substantially enriched in such cells can be then isolated to provide a stable cell line.

In the case of full recombinant human immunoglobulins, an important step is the selection of the specific isotype and constant region. Vectors specifically designed for expressing antibodies with the desired isotype and subtype (for example, human IgA, IgG1, IgG2, or IgG4) are widely described in the literature. Then, the full antibodies or the fusion proteins can be expressed as recombinant proteins in prokaryotic organisms (e.g. *Escherichia coli*; Sorensen H and Mortensen K, 2005; Venturi M et al., 2002), plants (Ma J et al., 2005), or eukaryotic cells, that allow a high level of expression as transient or stable transformed cells (Dinnis D and James D, 2005). This would be required in particular when the characterization of the antibodies has to be performed using more sophisticated assays, including in vivo assays, where the half-life of the antibody can be determined. The host cells can be further selected on the basis of the expression level of the recombinant protein.

In addition, when the protein is expressed, especially as an antibody, in eukaryotic host cells (mammalian cell lines, in particular), different vectors and expression systems have been designed for generating stable pools of transfected cell lines (Aldrich T et al., 2003; Bianchi A and McGrew J, 2003). High level, optimized, stable expression of recombinant antibodies has been achieved (Schlatter S et al., 2005), also due to optimization of cell culture conditions (Grunberg J et al., 2003; Yoon S et al., 2004) and by selecting or engineering clones with higher levels of antibody production and secretion (Bohm E et al., 2004; Butler M, 2005;).

The antibody, the antibody fragments, the bioactive peptide, the fusion protein, and any other protein defined above as being capable of binding and neutralizing hCMV can be purified using the well-established technologies that allow the isolation of either non-/recombinant proteins from cell culture or from synthetic preparations. These technologies should provide a sufficient amount of protein (from the microgram to the milligram range) to perform a more extensive characterization and validation for hCMV-related prophylactic, diagnostic, and therapeutic uses. To this purpose, the preparations of recombinant or natural proteins can be tested in in vitro or in vivo assays (biochemical, tissue- or cell-based assays, disease models established in rodents or primates, biophysical methods for affinity measurements, epitope mapping, etc.), in particular using any of those disclosed in the Examples or in literature for studying hCMV pathogenesis and immunobiology.

The antibodies, as purified preparations from human B cell supernatants or expressed as recombinant proteins, can be further validated using organ- or cell-based in vitro assays known in the literature (Eggers M et al. 1998; Lam V et al., 2006; Reinhardt B et al., 2003; Forthal D et al., 2001; Goodrum F et al., 2002). Moreover, relevant pre-clinical tests can be made in hCMV-infected animals, in particular in models where human host cells can be transplanted (Barry P et al., 2006; Gosselin J et al., 2005; Thomsen M et al., 2005).

The purification of the recombinant proteins of the invention can be carried out by any of the conventional methods known for this purpose, i.e. any procedure involving extraction, precipitation, chromatography, or the like. In particular, methods for antibody purification can make use of immobilized gel matrices contained within a column (Nisnevitch M and Firer M, 2001; Huse K et al., 2002; Horenstein A et al., 2003), exploiting the strong affinity of antibodies for substrates such Protein A, Protein G, or synthetic substrates (Verdoliva A et al., 2002; Roque A et al., 2004), or for specific antigens or epitopes (Murray A et al., 2002; Jensen L et al., 2004). After washing, the protein is eluted from the gel by a change in pH or ionic strength. Alternatively, HPLC (High Performance Liquid Chromatography) can be used. The elution can be carried out using a water-acetonitrile-based solvent commonly employed for protein purification.

The antibody, the antibody fragments, the bioactive peptides, the fusion proteins, and any other compound defined above using 26A1 antibody sequences can be used for detecting, treating, inhibiting, preventing, and/or ameliorating hCMV infection. To this purpose, such compounds can be used for preparing diagnostic, therapeutic, or prophylactic compositions for the management of hCMV infection.

In particular such compounds can be used for preparing pharmaceutical compositions, together with any pharmaceutically acceptable vehicle or carrier. These compositions may further comprise any additional therapeutic or prophylactic agent, such as vaccines, hCMV-neutralizing antibody, intravenous immunoglobulin preparations, immunomodulating compounds, and/or antiviral compounds. The literature provides some examples of such compounds acting on hCMV replication (Foscarnet, Vanganciclovir, Fomivirsen, or Ganciclovir) and already tested in humans, alone or in combination with intravenous immunoglobulin preparations (De Clercq E, 2003; Nigro G et al., 2005).

Moreover, recent literature suggests that human monoclonal antibodies can be used for supplementing (and replacing, if possible) present treatments such as intravenous immunoglobulin preparations and/or antiviral compounds, giving the opportunity to reduce frequency and/or dosage of such pharmaceutical compositions (Bayry J et al., 2007).

These compositions may comprise an antibody, an antibody fragment, a bioactive peptide, a fusion protein, and any other compound defined above on the basis of the sequence and activity of human 26A1 monoclonal antibody sequence. The compositions may further comprise a different hCMV-neutralizing antibody, an intravenous immunoglobulins (IVIg) preparation and/or an antiviral compound. The different hCMV-neutralizing antibody should be characterized by a different epitope, such as the ones already described in the literature or in the patent applications EP07114782, EP07115410, and EP07111741 (10B7, 8C10, and 1F7, respectively) that are associated to gH, gB, or other hCMV antigens. In fact, the literature shows many examples in which, when two or more antibodies directed to a viral or human target are combined in a pharmaceutical composition, the resulting composition may have an improved therapeutic efficacy due not to a simple additive effect but to a specific synergic effect (Logtenberg T, 2007).

The compositions comprising any of the proteins (e.g. antibodies, antibody fragments, fusion proteins, bioactive peptides) and of the nucleic acids defined above can be used and administered to an individual with a hCMV-related diagnostic, therapeutic, or prophylactic purpose. These compositions can be administered as means for hCMV-specific passive immunization which provide therapeutic compounds (in particular therapeutic antibodies or therapeutic antibodies fragments) that, by targeting hCMV virions, can inhibit the propagation of the virus in the treated patient, and potentially block the outbreak of a viral infection in the population.

Depending on the specific use, the composition should provide the compound to the human subject (in particular a pregnant woman or any other individual that is infected by hCMV or considered at risk for hCMV due to contact with an hCMV-infected individual) for a longer or shorter period of time. To this purpose, the composition can be administered, in single or multiple dosages and/or using appropriate devices, through different routes: intramuscularly, intravenously, subcutaneously, topically, mucosally, by a nebulizer or an inhaler, as eyedrops, in non-/biodegradable matrix materials, or using particulate drug delivery systems. In particular, the composition may allow topical or ocular administration, that represent a useful approach given the presence of hCMV in mucosae and eye. Moreover, antibodies and antibody fragments can be effective when applied topically to wounds (Streit M et al., 2006), cornea (Brereton H et al., 2005) or vagina (Castle P et al., 2002).

A pharmaceutical composition of the Invention should provide a therapeutically or prophylactically effective amount of the compound to the subject that allows the compound to exert its activity for a sufficient period of time. The desired effect is to improve the status of the hCMV patient by controlling hCMV infection, reactivation, and/or re-infection, and by reducing at least some of the clinical manifestations of hCMV infection, such as retinitis or pneumonitis (Landolfo S et al., 2003). For example, the composition should be administered at an effective amount from about 0.005 to about 50 mg/kg/body weight, depending on the route of administration, the number of administered doses, and the status of the individual.

In the case of compositions having diagnostic uses, the compound should be detected using technologies commonly established in the clinical and research laboratories for detecting virus in biological samples (e.g. ELISA or other serological assays), or, when administered to a subject in vivo, at least 1, 2, 5, 10, 24, or more hours after administration. The detection of hCMV can be performed, using the proteins of the invention, in substitution or coupled to the known means and procedures that have been established for monitoring chronic or acute hCMV infection in at risk populations of both immunocompetent and immunocompromised hosts, where a correlation between the data generated in vitro and the clinical status exists (Gilbert G, 2002; Gerna G and Lilleri D, 2006; Lazzarotto T et al., 2007).

A method for treatment, prophylaxis, or diagnosis of hCMV, or of hCMV-related disease can comprise the administration of a protein or of a nucleic acid as above defined. The method may further comprise the administration of a different hCMV-neutralizing antibody, an intravenous immunoglobulins (IVIg) preparation and/or an antiviral compound.

Clinical development and use should be based on the pharmacokinetics and pharmacodynamics of the antibody (Lobo E et al., 2004; Arizono H et al., 1994), the preclinical and clinical safety data (Tabrizi M and Riskos L, 2007), and the compliancy to international requirements for the production and quality control of monoclonal antibodies to be used for therapy and in vivo diagnosis in humans (Harris R et al. 2004).

The proteins of the invention can be also used for the preparation of a composition for detecting, treating, inhibiting, preventing, and/or ameliorating other, more widespread diseases (such as cardiovascular and autoimmune diseases, or some types of cancer) that can be defined as hCMV-related or hCMV-associated diseases. In these conditions, hCMV is considered as a possible cofactor since it is well-known that this virus is associated with cellular/immunological inflammatory processes (by stimulating the expression of Fc receptors, cell adhesion molecules, chemokines and cytokines), autoimmune activities (e.g. in atherosclerosis, restenosis) and with alterations to the antigen-presentation pathways (by inhibiting MHC class I and II expression) leading to cell apoptosis, differentiation, and migration, for example in blood vessels and in actively proliferating cells (Cinatl J et al., 2004; Soderberg-Naucler C, 2006b).

Moreover, hCMV infection has been also found associated to alteration of cellular metabolism (Munger J et al., 2007), depression (Phillips A et al., 2007), or risk factor for thrombotic events (Fridlender Z et al., 2007). Reactivation of hCMV and related complications has also been found in cancer patients (Sandherr M et al., 2006; Han X, 2007) or patients affected by inflammatory connective tissue diseases (Yoda Y et al., 2006), and in general in patients under immunosuppressive treatments such as corticosteroids (Yamashita M et al., 2006), or chemotherapy and other antibody-based immunosuppressive regimens (O'Brien S et al., 2006; Scheinberg P et al., 2007).

The invention will now be described by means of the following Examples, which should not be construed as in any way limiting the present invention.

EXAMPLES

Example 1

Production of Cell Cultures Secreting Human Monoclonal Antibodies that Neutralize hCMV Infectivity Materials & Methods
Selection of Human Donors that Present IgG Antibodies Neutralizing hCMV in the Blood Serum These hCMV-specific assays have been performed as outlined in PCT/EP2005/056871 or in the literature, as summarized below.

The hCMV-neutralizing antibodies were detected according to an hCMV microneutralization assay based on human Embryo Lung Fibroblasts (HELF cells) and hCMV AD169 strain (an hCMV laboratory strain from ATCC, cod. VR-538).

The hCMV microneutralization assays were also performed with the endotheliotropic hCMV VR1814 strain, a derivative of a clinical isolate recovered from a cervical swab of a pregnant woman (Revello M et al., 2001), and human umbilical vein endothelial cells (HUVEC). These cells were obtained by enzymatic treatment of umbilical cord veins and cultured in endothelial growth medium (EGM -2, Cambrex Bio Science) supplemented with 2% Foetal Bovine Serum (FBS), human recombinant vascular endothelial growth factor (VEGF), basic fibroblast growth factor (bFGF), human epidermal growth factor (hEGF), insulin growth factor (IGF-1), hydrocortisone, ascorbic acid, heparin, gentamycin and amphotericin B, (1 µg/ml each). Experiments were performed with cells at passage 2-6.

The use of HELF and HUVEC cells for studying hCMV infection and replication using clinical and laboratory strains has been described in many articles (Gerna G et al., 2002). In the present case, the cells were plated ($2.0$-$2.5 \times 10^4$/well) onto flat-bottom wells of a 96-well plate in 100 µl of Growth Medium, which contains Minimum Essential Medium (MEM; Gibco-BRL) with 10% Foetal Calf Serum (FCS), 1 mM sodium pyruvate (NaP), and GPS (2 mM glutamine, 100 U/ml penicillin and 100 µg/ml streptomycin). Cells were cultured for 24 hours at 37° C.

Fifty µl of antibody-containing samples (human serum, cell culture supernatants, or of Protein A-purified natural or recombinant IgG at indicated concentrations) were incubated with the laboratory strain hCMV AD169 [500 plaque forming units (pfu) in 50 µl of MEM with 5% FCS; total volume of the mixture was 100 µl] for 1 hour at 37° C. The mixture of antibody preparation and virus was then added to HELF cell monolayers (for hCMV AD169 and AL-1 strains) or HUVEC cell monolayers (for hCMV VR1814) and incubated for 1 hour. The Growth Medium was discarded from cell monolayers and replaced with the antibody-virus mixture. The plates were then centrifuged at 2,000 g for 30 minutes and incubated for 90 minutes at 37° C. in 5% $CO_2$. Growth Medium (100 µl) was added and the cultures were maintained in the incubator for a further 72 hours.

The effect of B cell supernatants on hCMV infectivity was measured by staining hCMV Intermediate Early Antigens (IEA, IE1+IE2) by indirect immunoperoxidase staining. The cell monolayers were fixed with acetone/methanol solution (stored at −20° C.) for 1 minute then washed with PBS. The cells were permeabilized in 0.1% Triton X-100 in PBS with 1% $H_2O_2$, 5 minutes on ice, then washed with PBS. Endogenous peroxidase was blocked with PBS with 50% methanol and 0.6% $H_2O_2$, 30 minutes at room temperature in the dark and then washed with PBS. Fifty µl of Protein Blocking Agent (Ultra Tech HRP 500-600 Test; Streptavidin-Biotin Universal Detection System; PN IM2391) were added for 10 minutes at room temperature, and then washed away with PBS. Mouse anti-HCMV IEA (clone E13; Argene Biosoft; ref. 11-003) was added to wells for 60 minutes at room temperature. After washing, cells were incubated with 50 µl of biotin-conjugated, secondary anti-human IgG (Ultra Tech HRP 500-600 Test; Streptavidin-Biotin Universal Detection System; PN IM2391) or peroxidase-conjugated goat anti-mouse IgG (Ultratech HRP).for 10 minutes. DAB substrate (Merck; no. 1.02924.0001) in 0.1% $H_2O_2$ was added for 30-45 minutes at 20° C. in the dark and the reaction stopped by dilution with PBS. IEA-positive nuclei were counted under the microscope.

Medium only or cell culture supernatants containing irrelevant IgG antibodies were used as a negative control. A commercial preparation of human IgG, purified from the serum of hCMV seropositive patients (Cytotect; Biotest), was used as a positive control with progressive dilutions, starting at 125 µg/ml. Positivity was defined as ≧40% inhibition of IEA-positive cells, compared to negative control wells.

The 50%-inhibition endpoint calculated using the Reed-Münch method will be considered the Neutralization Titre (NT):

NT=reciprocal antibody dilution [>50% inhibition]×
[(% inhibition greater than 50% -50%)/(% inhibition greater than 50% - % inhibition less than 50%)]

Selection of Human Donors on the Basis of the Presence in the Serum of IgG that Bind to Regions of the hCMV Envelope Glycoproteins gB or gH The hCMV-specific binding assays have been performed as outlined in PCT/EP2005/056871 or indicated by the Manufacturer, and validated with a commercial mixture of IgG antibodies specific for CMV (Cytotect; Biotest). The serum was tested in an ELISA specific for human IgG binding hCMV virion proteins that is commercially available (BEIA-CMV IgG Quant; Bouty, cod. 21465) and a gB (AD2) hCMV IgG ELISA, also commercially available (CG3 antigen Biotest AG, cod. 807035; FIG. 1A).

Briefly, breakable strips covered with an inactivated hCMV protein mixture (derived from the laboratory strain AD169) were placed into microplates and incubated with B cell supernatants diluted 1 : 81 (10 µl of supernatants added to 800 µl of sample diluents of the BEIA system), and the plate incubated at room temperature for 30 minutes. After a washing cycle, pre-diluted monoclonal anti-human IgG antibody conjugated with horseradish peroxidase (100 µl) was added and plate incubated at room temperature for a further 30 minutes. After a second washing cycle, pre-diluted substrate-TMB solution (100 µl) was added and the plate was incubated at room temperature for 15 minutes. The reaction was stopped using the Stop Solution (100 µl/well) and the optical density was measured in bi-chromatism at 450/620 nanometers.

Production of the Culture of Immortalized Human B Cells

Peripheral blood mononuclear cells (PBMCs) were obtained from a patient recovered from an acute hCMV infection (CMV7) selected because of the presence of hCMV-neutralizing antibodies in the serum. The EBV immortalization process to which PBMCs from CMV7 patient were subsequently exposed has been performed according to the teachings of PCT/EP2005/056871. Briefly, PBMCs were purified from peripheral blood by conventional density gradient centrifugation on Ficoll/Hypaque. CD22-positive cells were isolated from fresh PBMC (>90% purity) with anti-human CD22-coated beads by the VarioMACS technique (Miltenyi Biotec Inc.) as described by the manufacturer. The purified cells were stimulated with a combination of CpG2006 (Coley, 1 µg/ml) and IL-2 (Roche, 200U/ml). After a 4-day stimulation, cells were washed with fresh culture medium (RPMI-1640) and the B cells were highly enriched in IgG-positive cells with anti-human IgG-coated beads by using the VarioMACS technique (Miltenyi Biotec Inc.), following the manufacturer's instructions.

The selected and stimulated cells were suspended and maintained in RPMI-1640 cell culture medium supplemented with 10% (v/v) heat-inactivated FCS (Foetal Calf Serum), 1 mM sodium pyruvate, 100 µg/ml streptomycin and 100 U/ml penicillin, in 24-well plates at 37° C. and 5% CO2. The EBV immortalization was performed using B95.8 cell supernatant (1 : 1 v/v for 16 hours).

At the end of the process, the immortalized cells were washed with fresh culture medium (RPMI 1640 added with 10% Foetal Calf Serum) and put in culture for 3 weeks at a density of $1.5 \times 10^6$ cells/ml in 24 well plates with a feeder layer (irradiated allogeneic PBMC seeded at $5 \times 10^5$ cells/well), without CpG2006 (and not with CPG2006 as described in PCT/EP2006/069780 for the process started from PBMCs obtained from CMV5 donor).

Selection of Subcultures of Immortalized Human B Cells that Secrete hCMV Neutralizing Antibodies Fifteen days after exposure to EBV, the hCMV neutralizing activity was confirmed in the expanded, polyclonal cell culture with the AD169/HELF-based microneutralization assay described above. Then, the cells were seeded at 20 cells/well on irradiated (30 Gy), allogeneic PBMCs (50,000/well) in 100 µl IMDM added with 10% FCS and non essential amino acids (NEAA, diluted 1× from a 100× commercial stock solution; EuroClone) in the absence of CpG2006 and IL-2. A total of 4224 subcultures were generated and, after two weeks, 50 µl of the same medium were added. After a further 1-2 weeks of culture, the supernatants of cell cultures that presented growing and aggregated cells were tested in parallel using the hCMV neutralization assay based on HELF cells and hCMV strain AD169.

The supernatants of cell cultures that presented hCMV neutralizing activity were tested using the ELISAs for detecting binding of human IgG to regions of the gB hCMV envelope glycoprotein, or total hCMV proteins described above.

Alternatively, gB- or gH-based antigens were generated as Glutathione-S-Transferase (GST) fusion proteins. In the case of the gB(Ag)-GST antigen, the gB immunodominant region from hCMV strain C194 was fused to GST (BioDesign, Cat. No. R18102; GS-4B Sepharose Affinity purified, 1 mg/ml). In the case of gH(Ag)-GST antigen, the fragment of the gH glycoprotein of HCMV strain VR1814 was cloned by PCR, fused to GST gene, produced in E. coli and purified from the bacterial cell lysate on the basis of GST affinity. The recombinant gH(Ag)-GST antigen corresponds to an in-frame fusion between the gH amino terminal region (amino acids 16-144; FIG. 1B) from the hCMV strain VR1814 and GST. GST alone was used as negative control.

These ELISA were performed by applying a common ELISA protocol in a 96-well format with minor modifications. Briefly, the antigen is diluted at 2 µg/ml in PBS and 50 µl of this protein solution (containing 100 ng of the bacterially expressed fusion protein) was used for coating EIA polystyrene plates (Nunc; Cat No. 469949). The coating of ELISA plates was performed overnight at 4° C., then, after eliminating the protein solution, the plates were washed four times with 150 μl of Wash Buffer (PBS containing 0.05% of Tween20). A treatment for blocking unspecific binding was performed by then dispensing 100 μl PBS containing 1% of milk in each well for 1 hour at 37° C. After four washing cycles with 150 μl of Wash Buffer, 50 μl of supernatants from cell cultures were incubated in each well for 2 hours at 37° C., using 50 μl/well of the cell culture medium as negative control. After four washings cycles, 50 μl of the secondary antibody [goat anti-human IgG (Fc specific) antibody conjugated with horseradish peroxidase; diluted 1 : 30,000 in wash buffer; Sigma, Cat. No. A0170] were dispensed in each well and plates were incubated for 1 hour at room temperature. After four additional washing cycles, the enzymatic reaction was developed by adding 50 μl of Substrate-TMB (3,3',5,5' Tetramethylbenzidine; Sigma, Cat. No. T0440) in each well for further 30 minutes at room temperature. The chromogenic reaction was stopped by dispensing 100 μl of stop solution (1N Sulphuric acid) into each well and the optical density was read at 450 nm.

Results

Human PBMCs were obtained from an hCMV patient (CMV7) presenting a significant hCMV neutralization titre in serum (50% neutralization at 1 : 105 dilution), together with a strong reactivity in an ELISA (positive at 1 : 64 dilution a sample is considered positive for the presence of IgG anti-gB at ¼ or higher dilutions) based on the binding to the AD2 domains of glycoprotein B, one of the hCMV antigens best characterized as eliciting serum neutralizing antibodies (Qadri I et al., 1992; Kropff B et al., 1993), and cloned within the CG3 antigen (FIG. 1A). Moreover, the CMV7 sera was positive in another ELISA using the total hCMV virion proteins, where an activity of 74 AU/ml was measured (a sample is considered positive for the presence of anti-hCMV IgG when the result is at least 10 AU/ml)

B cells from the CMV7 patient were used for generating an immortalized, polyclonal cell culture highly enriched in B cells that secrete IgG using the EBV-based immortalization method disclosed in PCT/EP2005/056871 and PCT/EP2006/069780. Compared to this latter document, disclosing the selection of anti-hCMV antibodies from another donor (CMV5), the subcultures were prepared from the original bulk, polyclonal population of immortalized cells in the absence of CpG2006 and the supernatants were first selected for the presence of antibodies neutralizing hCMV infectivity by the microneutralization assay, and only after for antibodies binding to selected hCMV antigens.

The hCMV microneutralization assay was applied only to subcultures which proved to be actively growing with clusters of cells at 3 weeks of culture. The supernatants from the 324 wells were first screened in the hCMV neutralization assay, 20 supernatants among these were found to reduce the infectivity of hCMV AD169 strain by at least 40%. When characterizing the hCMV binding activities in these wells, only two were found positive for gB (either as CG3 antigen or a gB(Ag)-GST fusion protein), none for gH (as a gH(Ag)-GST fusion protein; FIG. 1B), and 18 wells for neither of them (FIG. 2).

Due to the low number of cells initially seeded in each well (20 cells/well), each subculture presenting hCMV-neutralizing activity, should likely produce monoclonal antibodies (i.e. secreted by cells clonally originated by a single, specific immortalized cell), especially given the low frequency of cells in the immortalized, polyclonal cell population that is expected to grow and secrete hCMV-neutralizing IgG. Further experimental activities were designed to confirm this assumption.

Example 2

Characterization of the 26A1 Antibody

Materials and Methods
Expansion and Characterization of the 26A1 Subculture

The cells from the original subculture 26A1 were expanded on irradiated allogeneic PBMC in IMDM medium (added with 10% FCS and NEAA), and the hCMV neutralizing activity was confirmed at least twice during this expansion step using the hCMV microneutralization assay, as described in Example 1 (see Table 1).

The amount of antibody secreted by the 26A1 subculture was determined at 24, 48, and 72 hours using a commercial quantitative human IgG ELISA kit (Immunotek; cod. 0801182; Zeptometrix Corp.) according to the manufacturer's instructions. The subclass of the 26A1 antibody was determined using a commercial assay (PeliClass human IgG subclass ELISA combi-kit; cod. #RDI-M1551cib, RDI Division of Fitzgerald Industries Intl.).

The cell culture was gradually expanded by seeding the cells contained in 1 well of a 96-well plate ($\approx 1 \times 10^5$) in one well of a 48 well plate on irradiated allogeneic PBMC in IMDM added with 5% FCS. After 5-7 days, cells were expanded in one well of a 24-well plate in the absence of feeder layer, in IMDM added with 5% FCS. Then, cells ($5 \times 10^5$/ml) were plated in a 6 well plate in the absence of feeder layer in 50% IMDM and 50% Hybridoma-SFM (Gibco, cod. 12045-084) added with 2.5% FCS. Cells were cultured in these conditions for at least one week. Exponentially growing cells were then washed and cultured in T75 Flasks in Hybridoma-SFM at a concentration ranging from $5 \times 10^5$ to $10^6$/ml. Cell culture supernatant was collected, the IgG quantified and purified on Protein A columns, dialyzed against PBS buffer and filtered (0.2 μM).

Characterization of the Antibody Secreted by the 26A1 Subculture

The BEIA-CMV, gB-based, and gH-based ELISA assays were described in Example 1 (FIGS. 1 and 2). The HSV assay was performed according to the literature (Laquerre S et al., 1998).

The hCMV plaque reduction assay was performed using the hCMV AD169 strain. Briefly, the virus was diluted to 1000 PFU/reaction. Equal amounts (0.1 ml) of virus and each antibody or cell culture supernatant were mixed and incubated at 37° C. for 1 hour. The mixtures were added to HELF cells monolayers (in 24-well plates) and allowed to adsorb for 1 hour at 37° C. Then the antibody-virus mixture was removed, and 1% methylcellulose overlayer-MEM-2% FCS was added to the infected cells. Plaques will be counted as a measure of infectivity at day 10 or 12 post-infection.

The 26A1 cell culture supernatant was tested in immunofluorescence on non-infected HELF or HUVEC cells. Briefly, cells ($7 \times 10^4$/ml) were seeded on gelatine-coated glass-coverslips in 24-well plates in MEM added with 10% FCS and then grown to semi-confluence. Cells were then washed twice with warm PBS, fixed with a pre-cooled (at −20° C.) mixture of 50% acetone/50% methanol for 1 minute at room temperature (RT) and then washed with PBS. Fixed cells were permeabilized with 0.2% Triton X-100 in PBS for 20 minutes on ice, washed with PBS and incubated for 15 minutes at RT with a blocking solution (PBS added with 2% FCS). Alternatively, fixed cells were not permeabilized to determine the capability of antibodies to recognize cell surface components. In this case, fixed cells were washed with PBS, incubated for 15 minutes at RT with a blocking solution (PBS added with 2% FCS) and incubated with 26A1 cell culture supernatant (80 μl), for 2 hours at 37° C. Cells were then washed with warm PBS (3 times) and incubated with 80 μl of FITC-conjugated rabbit anti-human IgG F(ab')2 (Jackson ImmunoResearch), to track the human IgG staining as green colour. The secondary antibodies were diluted 1 : 50 in PBS added with 0.05% Tween 80 and added to the cells for 1 hour at 37° C. in the dark. Then, cells were washed with warm PBS (3 times) and counter-stained with propidium iodide (0.25 μg/ml in PBS; Sigma). The coverslips were mounted on microscope-slide using the Mounting Medium (Vector Laboratories). Images were recorded with an Olympus Fluoview-IX70 inverted confocal laser scanning microscope.

Characterization of 26A1 IgG DNA/Protein Sequence and Recombinant Expression

An aliquot of the cell culture, resulting from the expansion of the initial 26A1 cell culture, was used for sequencing of the variable regions of heavy chain (VH) and light chain (VL) of 26A1 antibody according the technology established by Fusion Antibodies Ltd. Pellets of frozen cells (containing at least 50,000 cells) were used for extracting total RNA. The corresponding cDNA was produced by reverse transcription with an oligo(dT) primer. PCR reactions were set up to amplify VH region using a mix of IgG specific primers, and VL region with a mix of Igk/λ primers. The PCR products of two amplification reactions were cloned using a Eco RI restriction site in a sequencing vector (pCR2.1; Invitrogen) and used for transforming TOP10 E. coli cells.

At least ten selected colonies obtained from the two transformations were picked and analyzed by sequencing. The resulting DNA sequences were aligned and translated into protein sequence generating a consensus DNA and protein sequence for VH 26A1 (SEQ ID NO. : 4 and SEQ ID NO. : 5, respectively) and VL 26A1 (SEQ ID NO. : 9 and SEQ ID NO. : 10, respectively). The VH 26A1 and VL 26A1 protein sequences were compared and aligned with sequences present in databases in the public domain (using GenomeQuest, GeneSeq, and EBI databases). The CDRs characterizing VH 26A1 (SEQ ID NO. : 5, 7, and 8) and VL 26A1 (SEQ ID NO. : 11, 12, and 13) protein sequences were predicted by the IMGT database (Giudicelli V et al., 2004).

Recombinant human 26A1 monoclonal antibody was expressed in eukaryotic cells by cloning the consensus 26A1 heavy and light chain variable region sequences in the same expression vector, already containing the corresponding constant regions (for human IgG1 heavy chain and human Ig lambda chain), and a dual promoter vector allowing expression of both antibody chains. The complete sequence of recombinant human 26A1 monoclonal antibody in the vector was confirmed by DNA sequencing and used to transiently transfect CHO DG44 cells (Derouazi M et al., 2006) that were adapted to grow in serum-free suspension culture and seeded at $1\times10^6$ cells per ml in a 125 ml spinner flask. The transfection was performed with a mixture of 300 μg of expression vector with 900 μg of linear 25 kDa poly(ethylenimine). Cells were incubated at 37° C. in 5% $CO_2$ for 6 days in the spinner flask before the media was harvested. The recombinant antibody was purified using a Protein G column on an Akta Prime chromatography unit following the manufacturer's standard programme.

Results

Amongst the subcultures containing growing and IgG-secreting cells, the cell culture supernatants of a few of them contained antibodies that neutralize hCMV infection but did not present a significant binding to the specific recombinant antigens gB and gH tested by ELISA (FIGS. 1 and 2). In particular, the 26A1 subculture, that secretes an IgG1, showed the stronger and more reproducible hCMV neutralization activity, and it was chosen for a more detailed molecular and biological characterization.

The binding of the IgG present in the supernatant from 26A1 subculture to hCMV was confirmed using an ELISA containing a mixture of hCMV proteins (BEIA-CMV). At the same time, this supernatant showed a significant hCMV neutralizing activity against different hCMV strains in two human host cell systems (as shown in Table 1). This activity was not observed when the supernatant was used in a HSV-specific neutralization assay.

Moreover, the 26A1 subculture has been expanded and further subcloned at 10 cells/well to confirm its monoclonality in terms of expression of hCMV-neutralizing, human IgG1. In fact, amongst the wells showing cell growth, all displayed a neutralizing activity ranging from 50 to 98% in the original AD169-based assay, confirming the results obtained with the original 26A1 subculture.

The cells in the original 26A1 subculture were used for scaling-up IgG production, generating progressively larger cultures from which IgG can be purified and tested in hCMV assays. Larger cultures were generated by gradually expanding 26A1 culture and eliminating some requirements for growth in cell culture (such as feeder layer, Foetal Calf Serum). Using this approach, it was demonstrated that larger cell cultures generated from the original 26A1 subculture secrete IgG1 at a concentration of approx. 16 μg/ml/$10^6$ cells. These larger cultures showed a doubling time of 4 days, even in the absence of feeder layer, and the hCMV neutralizing activity was maintained in culture for more than 2 months.

Figure 3:
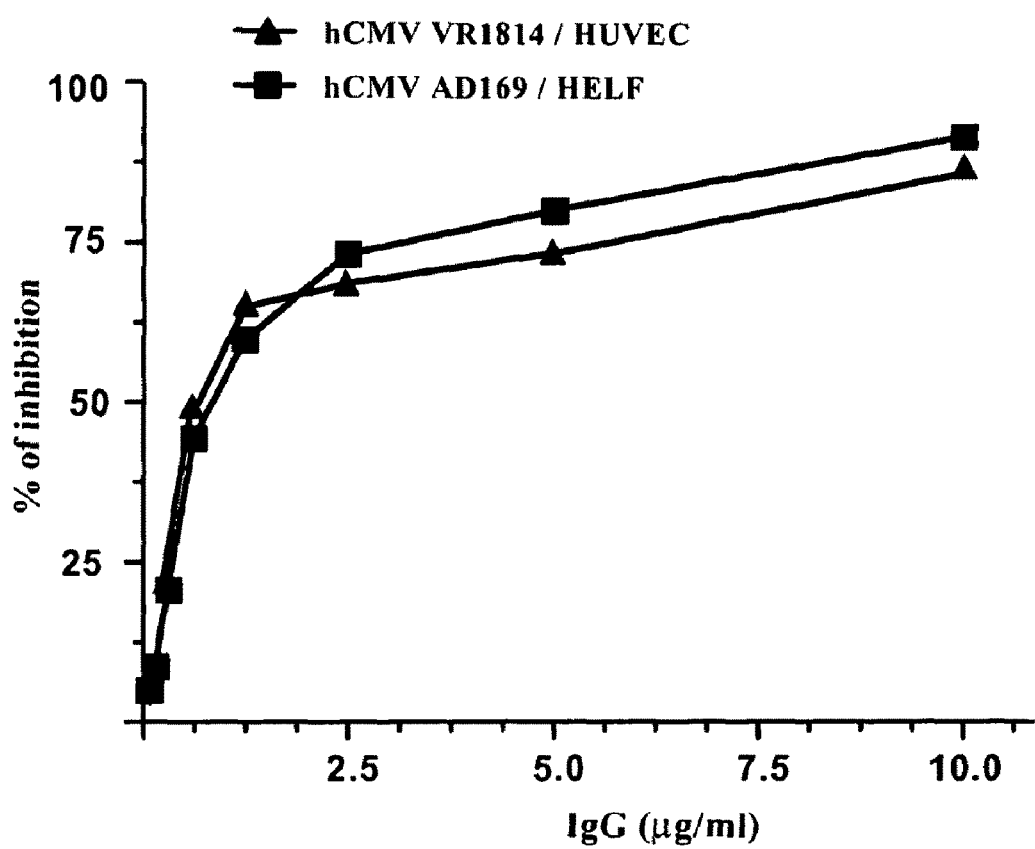
FIG. 3: hCMV neutralizing activity of the natural 26A1 antibody, as purified by affinity chromatography using Protein A from the supernatant of a 26A1 subculture-derived cell culture maintained in serum-free medium. The dose-response curve was performed in the hCMV neutralization assay including either human embryonic fibroblasts (HELF) together with the hCMV strain AD169 (1,000 PFU/reaction; IC50 0.82 µg/ml), or human umbilical vein endothelial cells (HUVEC) together with the hCMV strain VR1814 (1,000 PFU/reaction; IC50 0.67 µg/ml).

The hCMV neutralization assays were repeated with the 26A1 antibody, in the form of human IgG purified by affinity chromatography from large cell culture. The 26A1 IgG was tested in dose-response experiments to assess the concentration required for 50% inhibition (inhibitory concentration 50, or IC50) of hCMV infectivity, using two assays with different combinations of hCMV strains and human target cells. The results showed that the potent neutralizing activity of the Protein A-purified natural 26A1 IgG is neither cell-type nor virus-strain specific, and can be evaluated quantitatively as providing IC50 values of approx. 1 μg/ml and a neutralizing effect approaching 100% in both assays (FIG. 3).

When comparing the neutralizing activity of the Protein A-purified natural 26A1 IgG with that of a commercial preparation of hyperimmune IgG (IVIg) against hCMV (Cytotect, Biotest) against the clinical isolate in HUVEC cells, the IC50 of 26A1 is 25 fold lower than that required for this commercial preparation, demonstrating the potent neutralizing activity of 26A1 antibody.

In order to exclude that the neutralizing activity present in the supernatant from the 26A1 subculture is due to the binding to a cell surface molecule, the supernatant was tested in immunofluorescence with uninfected HELF or HUVEC cells. This assay showed that the IgG1 produced by 26A1 culture does not bind to the uninfected human cells. When the same cell supernatant is tested in ELISA against relevant hCMV antigens, the antibody does not bind such proteins (FIG. 4), indicating that the 26A1 antibody likely recognizes another, undetermined antigen on the hCMV envelope inducing the production of neutralizing antibodies.

The monoclonality of the hCMV neutralizing antibody secreted in the 26A1-derived cell cultures was further confirmed by sequencing IgG-specific PCR products obtained from this cell culture. Cell pellets were prepared for RNA extraction and reverse transcription using cells originated from 26A1 subculture. The resulting cDNA was then used for amplifying VH and VL sequences using specific primers for the variable regions of human IgG heavy and light chains, respectively. The PCR products were then cloned in plasmids that were used for transforming bacterial cells. Bacterial transformants were randomly picked and used for sequencing the cloned PCR products. All the clones showed the same DNA sequence, apart from minor differences possibly due to PCR-induced error, allowing the determination of consensus sequences and CDRs for the variable regions of the heavy chain (FIG. 5) and light chain (FIG. 6) of the human 26A1 monoclonal antibody.

The sequences encoding the VH and VL regions of the 26A1 antibody can be re-cloned in expression vectors for the appropriate expression of 26A1 variable regions as an antibody fragment (Fab or ScFv) or within a fully human, recombinant antibody having a specific isotype and subclass (e.g. IgA, IgG1, or IgG4). These recombinant antibodies can than be tested for confirming the specific hCMV neutralizing activity in the appropriate assays.

The recombinant human 26A1 monoclonal antibody was produced in eukaryotic cells as a recombinant human IgG1 by cloning the DNA encoding the heavy chain (FIG. 7) and light chain (FIG. 8) in an appropriate expression vector that has been used for transfecting CHO cells in transient expression experiments. The recombinant human 26A1 monoclonal antibody was affinity purified by cell culture supernatants and tested in different assays for hCMV neutralization. The tests were performed with the AD169/HELF cells system in both microneutralization and plaque reduction assay. The recombinant human 26A1 monoclonal antibody efficiently neutralized hCMV infectivity in a manner comparable with the Protein A-purified natural 26A1 antibody with a calculated IC50 of approx. 1 µg/ml (FIG. 9). The tests were pursued also in neutralization and plaque reduction assays based on different combinations of hCMV strains and target cells, all confirming the comparable efficacy of both natural and recombinant human 26A1 monoclonal antibody (FIG. 10).

Thus, the 26A1 antibody, in the form of either natural or recombinant human monoclonal antibody, is an antibody that can be used for the clinical management of hCMV infection and of an hCMV-related disease.

TABLE 1

| hCMV Strain | Human Cell Line | Inhibition of hCMV infection using 26A1 cell culture supernatant [a] |
|---|---|---|
| AD169 [b] | HELF | ++++ |
| VR1814 [c] | HELF | ++ |
| AL-1 [d] | HELF | +++ |
| VR1814 [c] | HUVEC | ++++ |

[a] +, ++, +++, and ++++ correspond to 20-40%, 41-60%, 61-80%, and more than 80% of inhibition of the hCMV infection, respectively
[b] hCMV laboratory strain (from ATCC, code VR-538)
[c] an endothelial cell-tropic derivative of a clinical isolate recovered from a cervical swab of an hCMV-infected pregnant woman (Revello M et al., 2001)
[d] derivative of a clinical isolate recovered from a bronchoalveolar lavage fluid of an hCMV-infected lung transplant recipient (Luganini A et al., unpublished)

References

Aldrich T et al., (2003). Biotechnol Prog. 19 : 1433-8.
Arizono H et al., (1994). Arzneimittelforschung. 44 : 909-13.
Baldanti F and Gerna G, (2003). J Antimicrob Chemother. 52 : 324-30.
Barrios Y et al., (2004). J Mol Recognit. 17 : 332-8.
Barry P et al., (2006). ILAR J. 47 : 49-64.
Bayry J et al., (2007). Nat Clin Pract Neurology. 3 : 120-1.
Bendtsen J et al., (2004). J Mol Biol. 340 : 783-95.
Bianchi A and McGrew J (2003). Biotechnol Bioeng. 84 : 439-44.
Boeckh M et al., (2001). Biol. Blood Marrow Transplant. 7 : 343-351.
Bohm E et al., (2004). Biotechnol Bioeng. 88 : 699-706.
Bonaros N et al., (2004). Transplantation. 77 : 890-7.
Bond C et al., (2003). J Mol Biol. 332 : 643-55.
Brereton H et al., (2005). Br J Ophthalmol. 89 : 1205-9.
Britt W and Mach M, (1996). Intervirology. 39 : 401-12.
Butler M, (2005). Appl Microbiol Biotechnol. 68 : 283-91.
Carton J et al., (2007). Protein Expr Purif. 55 : 279-86.
Castle P et al., (2002). J Reprod Immunol. 56 : 61-76.
Chapman A et al., (1999). Nat Biotechnol. 17 : 780-3.
Chatenoud L, (2005). Methods Mol Med. 109 : 297-328.
Cinatl J et al., (2004). FEMS Microbiol Rev. 28 : 59-77.
Coaquette A et al., (2004). Clin Infect Dis. 39 : 155-61.
Dar L, (2007). Indian J Med Res. 126 : 99-100.
De Clercq E, (2003). J Antimicrob Chemother. 51 : 1079-83.
Derouazi M et al., (2006). Biochem Biophys Res Commun. 340 : 1069-77.
Dinnis D and James D, (2005). Biotechnol Bioeng. 91 : 180-9.
Dunman P and Nesin M, (2003). Curr Opin Pharmacol. 3 : 486-96.
Eggers M et al., (1998). J Med Virol. 56 : 351-8.
Fang J et al., (2005). Nat Biotechnol. 23 : 584-90.
Forthal D et al., (2001). Transpl Infect Dis. 3 (Suppl 2) : 31-4.
Fridlender Z et al., (2007). Amer J Med Sci. 334 : 111-4.
Furebring C et al., (2002). Mol Immunol. 38 : 833-40.
Gandhi M and Khanna R, (2004). Lancet Infect Dis. 4 : 725-38.
Gerna G et al., (2002). J Clin Microbiol. 40 : 233-8.
Gerna G and Lilleri D, (2006). Herpes. 13 : 4-11.
Gicklhorn D et al., (2003). J Gen Virol. 84 : 1859-62.
Gilbert G, (2002). Med J Aust. 176 : 229-36.
Gilbert C and Boivin G, (2005). Antimicrob Agents Chemother. 49 : 873-83.
Gilliland L et al., (1996). Tissue Antigens. 47 : 1-20.
Gilpin A et al., (2003). Control Clin Trials. 24 : 92-8.
Giudicelli V et al., (2006). Nucleic Acids Res. 34: D781-4.
Goodrum F et al., (2002). PNAS. 99 : 16255-60.
Gosselin J et al., (2005). J Immunol. 174 : 1587-93.
Greijer A et al., (1999). J Clin Microbiol. 37 : 179-88.
Griffiths P, (2004). Herpes. 11 (Suppl 2) : 95A-104A.
Griffiths P and Walter S, (2005). Curr Opin Infect Dis. 18 : 241-5.
Grote A et al., (2005). Nucleic Acids Res. 33: W526-31.
Grunberg J et al., (2003). Biotechniques. 34 : 968-72.
Hamrock D, (2006). Int Immunopharmcology. 6 : 535-42.
Han X, (2007). J Clin MIcrob. 45 : 1126-32.
Harris R et al., (2004). Drug Development Research. 61 : 137-154.
Hebart H and Einsele H, (2004). Hum Immunol. 65 : 432-6.
Horenstein A et al., (2003). J Immunol Methods. 275 : 99-112.
Huse K et al., (2002). J Biochem Biophys Methods. 51 : 217-31.
Jain M et al., (2007). Trends Biotechnol. 25 : 307-16.
Jensen L et al., (2004). J Immunol Methods. 284 : 45-54.
Kalil A et al., (2005). Ann Intern Med. 143 : 870-80.
Keller M and Stiehm E, (2000). Clin Microbiol Rev. 13 : 602-14.
Kim S et al., (2005). Mol Cells. 20 : 17-29.
Kiss C et al., (2006). Nucleic Acids Res. 34: e132.
Klein M et al., (1999). J Virol. 73 : 878-86.

Klenovsek K et al., (2007). Blood. 110 : 3472-9.
Knappik A et al., (2000). J Mol Biol. 296 : 57-86.
Kocher A et al., (2003). J Heart Lung Transpl. 22 : 250-7.
Kropff B et al., (1993). J Med Virol. 39 : 187-95.
Kruger R et al., (2003). J Heart Lung Transpl. 22 : 754-63.
Ladner R, (2007). Nature Biotechnol. 25 : 875-77.
Laffly E and Sodoyer R, (2005). Hum Antibodies. 14 : 33-55.
Lam V et al., (2006). Biotechnol Bioeng. 93 : 1029-39.
Landolfo S et al., (2003). Pharmacol Ther. 98 : 269-97.
Laquerre S et al., (1998). J Virol. 72 : 6119-6130.
Lazzarotto T et al., (2007). J. Clin Vir. Doi : 10.1016/j.jcv.2007.10.015.
Levi M et al., (2000). AIDS Res Hum Retroviruses. 16 : 59-65.
Lobo E et al., (2004). J Pharm Sci. 93 : 2645-68.
Logtenberg T, (2007). Trends Biotechnol. 25 : 390-4.
Ma J et al., (2005). Vaccine. 23 : 1814-8.
Mantis N et al., (2007). J Immunol. 179 : 3144-52.
McLean G et al., (2006). Mol Immunol. 43 : 2012-22.
Marasco W and Sui J, (2007). Nat Biotechnol. 25 : 1421-34.
Marshall G et al., (2000). Viral Immunol. 13 : 329-41.
Matsumoto Y et al., (1986). Bioch Biophy Res Commun. 137 : 273-280.
Munger J et al., (2007). PLoS Pathogens. 2 : 1165-1175.
Murray A et al., (2002). J Chromatogr Sci. 40 : 343-9.
Nilsson J et al., (1997). Protein Expr Purif. 11 : 1-16.
Navarro D et al., (1997). J Med Virol. 52 : 451-9.
Nigro G et al., (2005). N Engl J Med. 353 : 1350-62.
Nilsson J et al., (1997). Protein Expr Purif. 11 : 1-16.
Nisnevitch M and Firer M, (2001). J Biochem Biophys Methods. 49 : 467-80.
O'Brien S et al., (2006). Clin Lymphoma Myeloma. 7 : 125-30.
Ohlin M et al., (1993). J Virol. 67 : 703-10.
Phillips A et al., (2007). Brain Behav Immun. Doi : 10.1016/j.bbi.2007.06.012.
Puius Y and Snydman D, (2007). Curr Opin Infect Dis. 20 : 419-24.
Qadri I et al., (1992). J Gen Virol. 73 : 2913-21.
Rasmussen L et al., (1991). J Infect Dis. 164 : 835-42.
Reinhardt B et al., (2003). J Virol Methods. 109 : 1-9.
Revello M et al., (2001). J Infect Dis. 184 : 1078-81.
Rojas G et al., (2004). J Immunol Methods. 293 : 71-83.
Roque A et al., (2004). Biotechnol Prog. 20 : 639-5.
Rothe M et al., (2001). J Med Virol. 65 : 719-29.
Sandherr M et al., (2006). Ann Oncol. 17 : 1051-9.
Scheinberg P et al., (2007)Blood. 109 : 3219-24.
Schlatter S et al., (2005). Biotechnol Prog. 21 : 122-33.
Schleiss M, (2003). Herpes. 10 : 4-11.
Schleiss M, (2005). Herpes. 12 : 66-75.
Schoppel K et al., (1996). Virology. 216 : 133-45.
Schrader J and McLean G, (2007). Immunol Lett. 112 : 58-60.
Shimamura M et al., (2006). J Virol. 80 : 4591-600.
Simpson J et al., (1993). J Virol. 67 : 489-96.
Smith J et al., (1995). J Biol Chem. 270 : 30486-30490.
Snydman D, (2006). Rev Med Virol. 16 : 289-95.
Soderberg-Naucler C, (2006a). Crit Rev Immunol. 26 : 231-64.
Soderberg-Naucler C, (2006b). J Intern Med. 259 : 219-46.
Sorensen H and Mortensen K, (2005). Microb Cell Fact. 4 : 1.
Streit M et al., (2006). Int Wound J. 3 : 171-9.
Tabrizi M and Riskos L, (2007). Drug Disc Today. 12 : 540-7.
Thomsen M et al., (2005). Tissue Antigens. 66 : 73-82.
Urban M et al., (1992). J Virol. 66 : 1303-11.
Venturi M et al., (2002). J Mol Biol. 315 : 1-8.
Verdoliva A et al., (2002). J Immunol Methods. 271 : 77-8.
Xu J and Davis M, (2000). Immunity. 13 : 37-45.
Wang D and Shenk T, (2005). Proc Natl Acad Sci USA. 102 : 18153-8.
Wang X et al., (2005). Nature Med. 11 : 515-521.
Watkins N et al., (2004). Tissue Antigens. 63 : 345-54.
Weber B et al., (1993). Clin Investig. 71 : 270-6.
Wiegand T and Young L, (2006). Int Ophthalmol Clin. 46 : 91-110.
Wijkhuisen A et al., (2003). Eur J Pharmacol. 468 : 175-82.
Yamashita M et al., (2006). Clin Exp Rheumatol. 24 : 649-55.
Yoda Y et al., (2006). Mod Rheumatol. 16 : 137-42.
Yoon S et al., (2004). Biotechnol Prog. 20 : 1683-8.

The invention claimed is:

1. An isolated protein comprising the amino acid sequences as set out in SEQ ID NO: 5 and SEQ ID NO: 10.

2. The protein of claim 1, wherein said protein is an antibody, an antibody fragment, a bioactive peptide, or a fusion protein.

3. The protein of claim 2, wherein said antibody is a human recombinant antibody.

4. The protein of claim 3, wherein said antibody comprises a heavy chain having the protein sequence set out in SEQ ID NO.: 15, and a light chain having the protein sequence set out in SEQ ID NO.: 17.

5. The protein of claim 2, wherein said antibody fragment is a variable heavy/light chain heterodimer, or a single-chain fragment variable.

6. The protein of claim 1, wherein said protein binds and neutralizes human Cytomegalovirus (hCMV).

7. An isolated nucleic acid encoding the protein of claim 1.

8. The nucleic acid of claim 7, wherein said nucleic acid comprises a sequence having at least 90% identity with SEQ ID NO.: 4 and further comprises a sequence having at least 90% identity with SEQ ID NO.: 9.

9. A vector comprising the nucleic acid of claim 7.

10. An isolated prokaryotic or eukaryotic host cell comprising the nucleic acid of claim 7.

11. The host cell of claim 10 wherein said cell secretes the protein of claim 1.

12. A therapeutic, prophylactic, or diagnostic composition for hCMV infection or for an hCMV-related disease, comprising the protein of claim 1, or the nucleic acid of claim 7.

13. The composition of claim 12 wherein the composition is formulated for ocular or topical administration.

14. The composition of claim 12, further comprising a different hCMV-neutralizing antibody, an intravenous immunoglobulins preparation and/or an antiviral compound.

15. A method for treatment of hCMV infection, or of a hCMV-related disease, comprising administering the protein of claim 1 or the nucleic acid of claim 7 to an individual with an hCMV infection or hCMV-related disease in a therapeutically effective amount, wherein administering inhibits propagation of hCMV in the individual.

16. The method of claim 15 further comprising administering a different hCMV-neutralizing antibody, intravenous immunoglobulins preparation and/or an antiviral compound.

17. A method for hCMV prophylaxis, or hCMV-related disease prophylaxis, comprising administering the protein of claim 1 or the nucleic acid of claim 7 to an individual in a prophylactically effective amount, wherein administering results in inhibition or prevention of hCMV infection.

18. The method of claim 17 further comprising the administration of a different hCMV-neutralizing antibody, intravenous immunoglobulins preparation and/or an antiviral compound.

19. A method of diagnosing hCMV infection, or hCMV-related disease, comprising contacting a sample from an individual with the protein of claim 1 and detecting binding of the protein with hCMV, wherein detecting binding of the protein to hCMV in the sample is indicative of hCMV infection in an individual from whom the sample was obtained.

20. The method of claim 19 further comprising contacting the sample with a different hCMV-neutralizing antibody and/or an intravenous immunoglobulins preparation.

* * * * *

UNITED STATES PATENT AND TRADEMARK OFFICE
CERTIFICATE OF CORRECTION

| | | |
|---|---|---|
| PATENT NO. | : 8,153,129 B2 | Page 1 of 1 |
| APPLICATION NO. | : 12/519236 | |
| DATED | : April 10, 2012 | |
| INVENTOR(S) | : Ada Funaro et al. | |

It is certified that error appears in the above-identified patent and that said Letters Patent is hereby corrected as shown below:

On the Title page, Item (54) and in the Specification, Column 1, line 2, "CYTIMEGALOVIRUS" should be -- CYTOMEGALOVIRUS --.

Signed and Sealed this
Eighteenth Day of November, 2014

Michelle K. Lee
*Deputy Director of the United States Patent and Trademark Office*